United States Patent [19]

Shirai et al.

[11] 4,112,434
[45] Sep. 5, 1978

[54] BIORHYTHM CHART DRAWING-UP APPARATUS

[75] Inventors: Yujiro Shirai, No. 4-9 Sugamo 3-chome, Toshima-ku; Akinori Satake, both of Tokyo, Japan

[73] Assignee: Yujiro Shirai, Tokyo, Japan

[21] Appl. No.: 831,158

[22] Filed: Sep. 7, 1977

[30] Foreign Application Priority Data

Sep. 10, 1976 [JP] Japan .................. 51-108448

[51] Int. Cl.² .................. G01D 9/00; G01D 9/28; A61B 5/00
[52] U.S. Cl. .................. 346/33 ME; 346/49; 128/2 R
[58] Field of Search .......... 346/33 ME, 49; 128/1 R, 128/2 R

[56] References Cited

U.S. PATENT DOCUMENTS 2,202,935  6/1940  Weiss .................. 346/33 ME X
4,033,336  7/1977  Murawski et al. ......... 346/33 ME X

FOREIGN PATENT DOCUMENTS 339,758  9/1959  Switzerland.

Primary Examiner—George H. Miller, Jr.
Attorney, Agent, or Firm—Bernard Malina

[57] ABSTRACT

Pulse motors rotating at periods corresponding to physical rhythm, rhythm of sentiment and rhythm of intellect are provided and discs having a pin eccentrically extending are coupled, respectively, with output axes of pulse motors so as to convert rotation movement into reciprocation movement through T-shaped piston rods. Plungers having ball point pens are respectively provided on the T-shaped piston rods. Data put in by digital switches are stored and calculated by the guide number to determine rotation angle of the pulse motors to set the ball point pens at the starting position. At the first recording area for the first date of a month arriving below the ball point pen, the pulse motors are initiated in their rotation from the starting position within a proper period thereof and a coil is energized so that the ball point pen will come in contact with the recording paper for drawing up the biorhythm chart.

3 Claims, 25 Drawing Figures

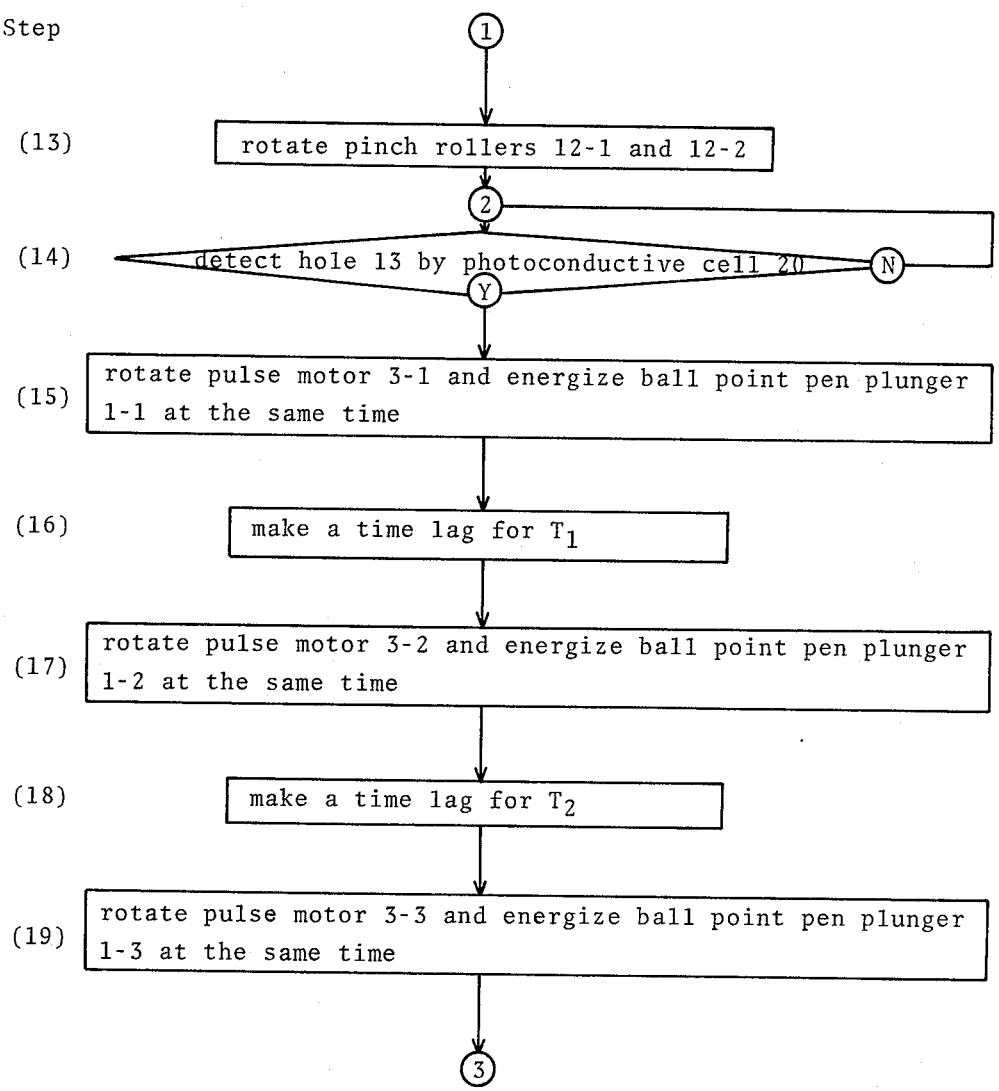

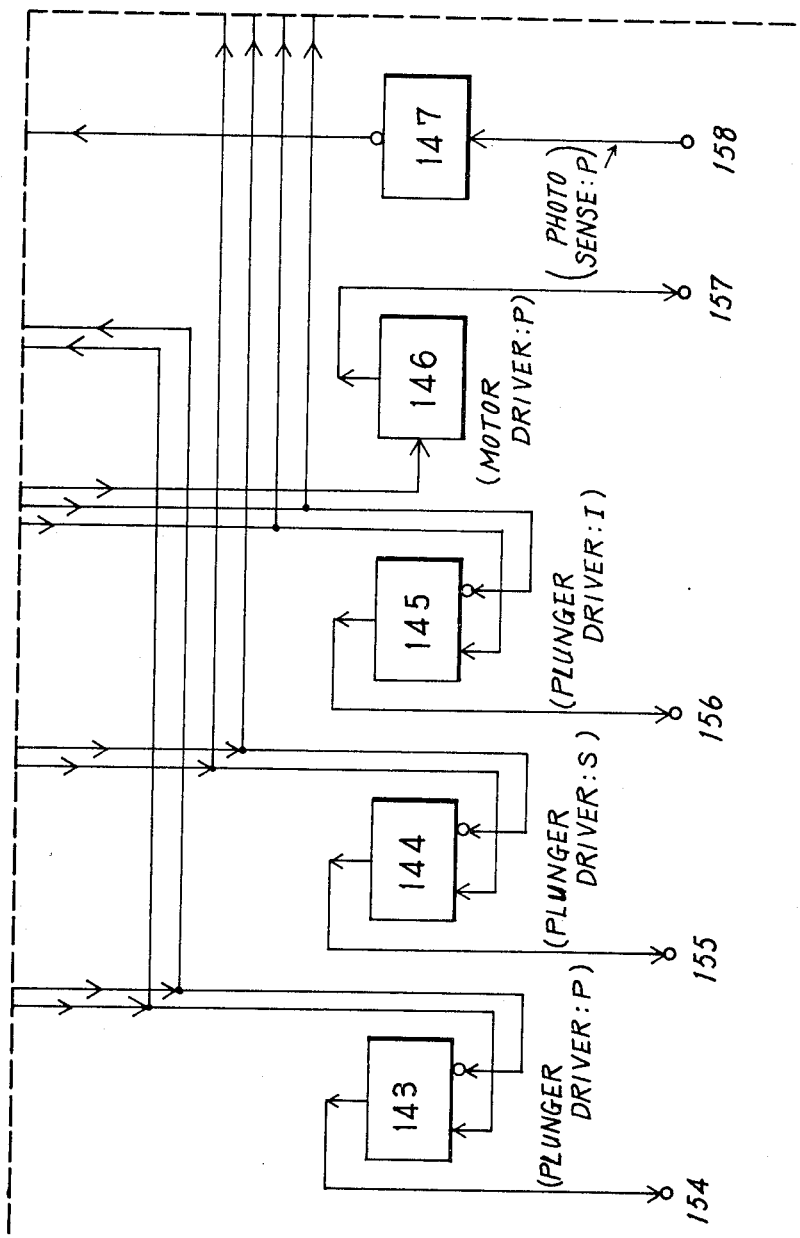

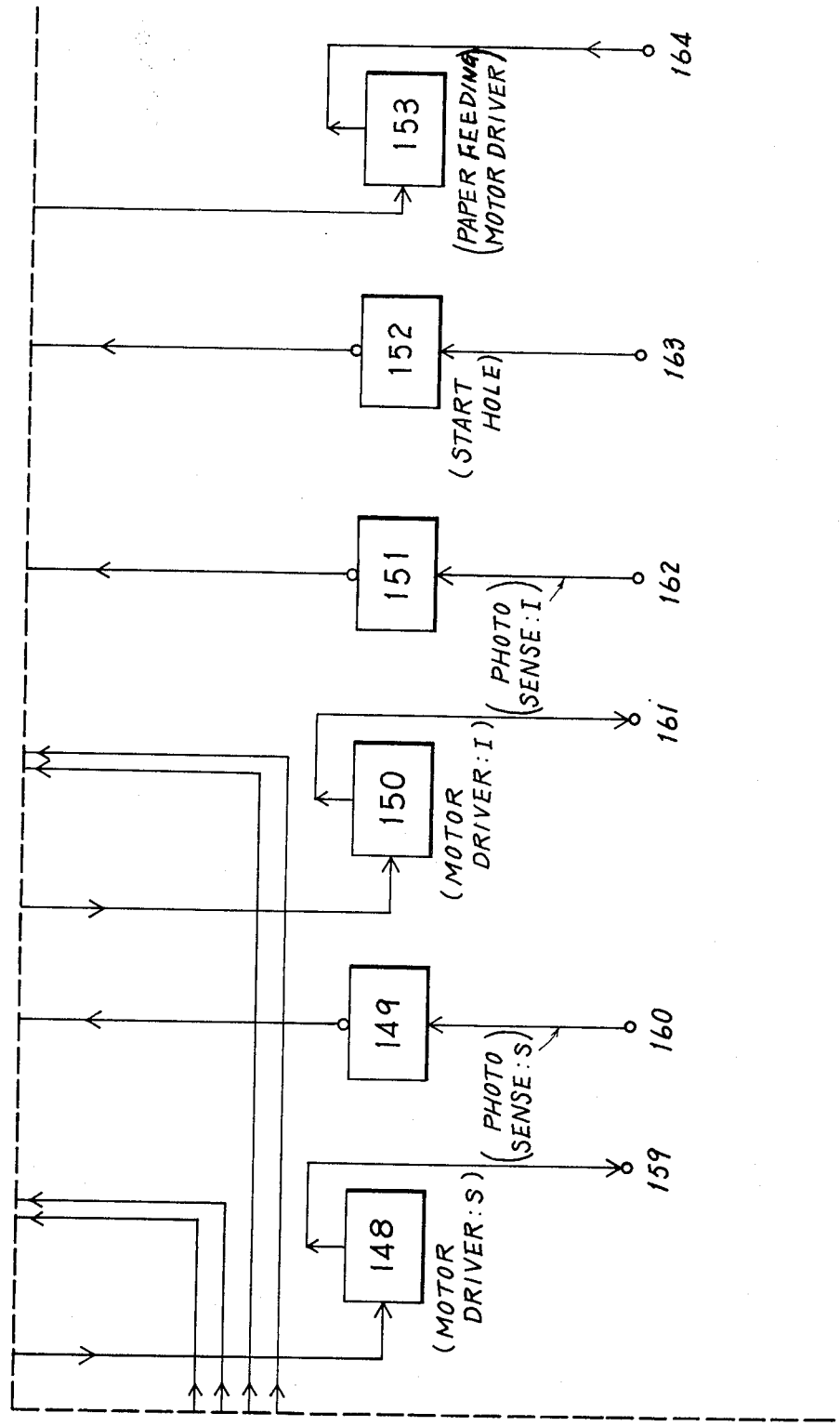

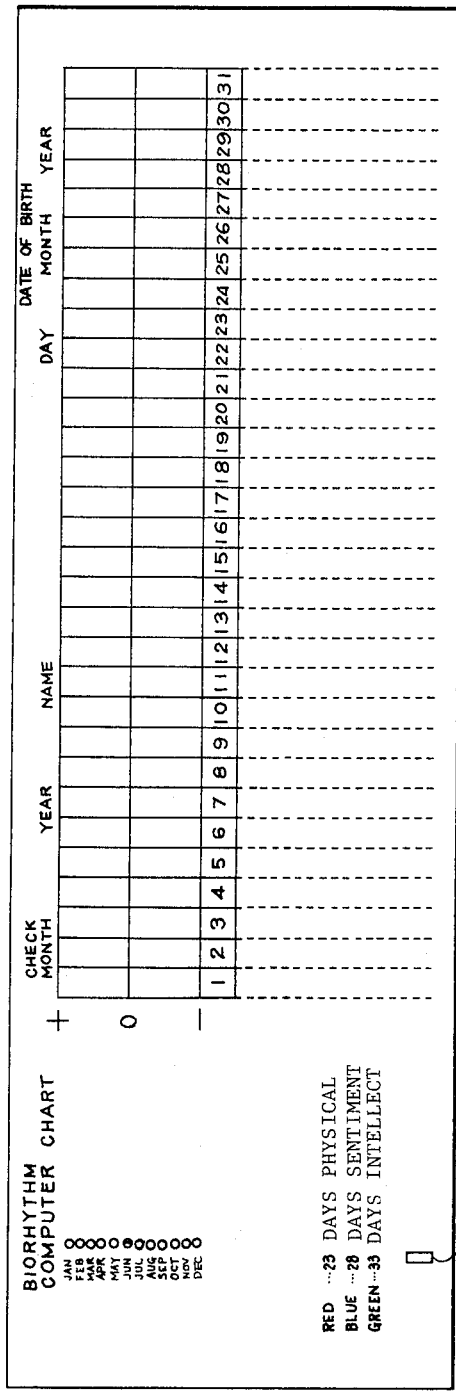

Fig. 9 A
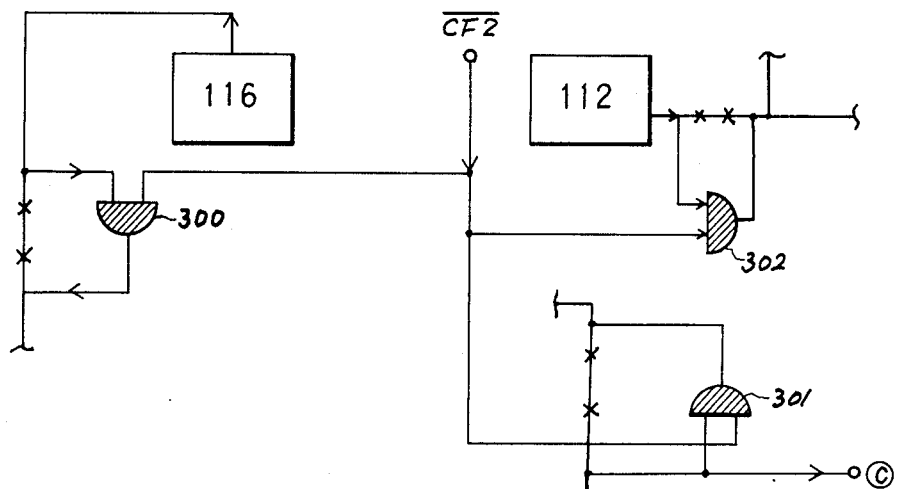
Fig. 9 C
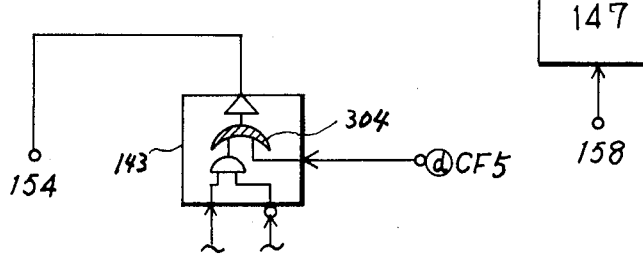
Fig. 9 D
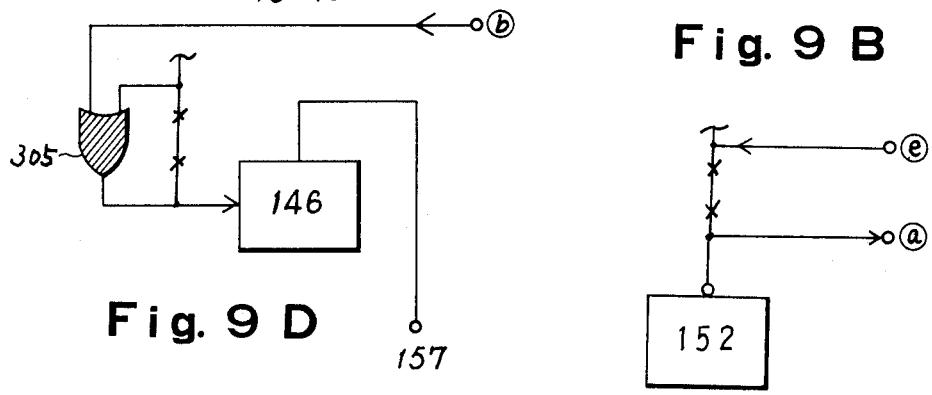
Fig. 9 B

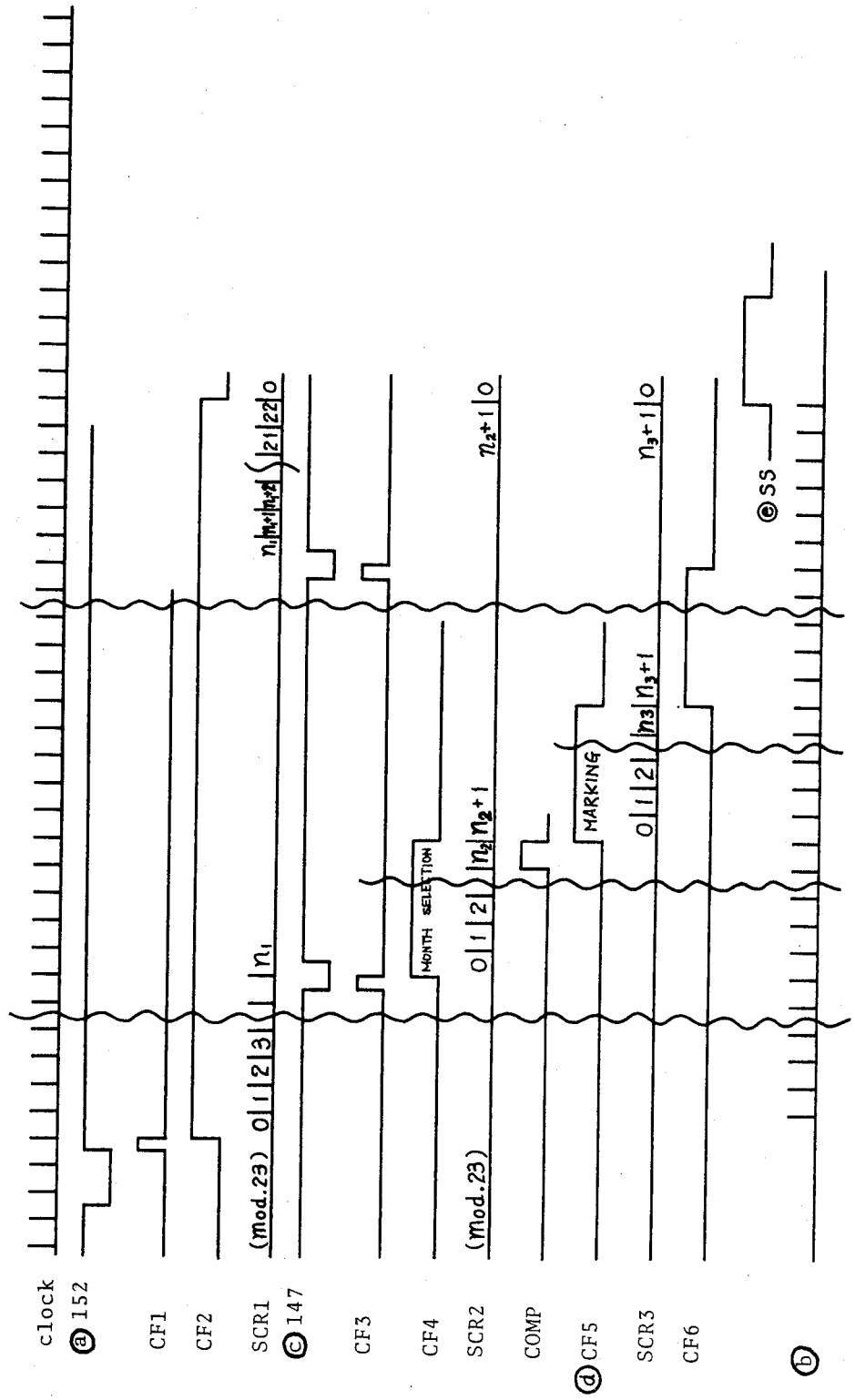

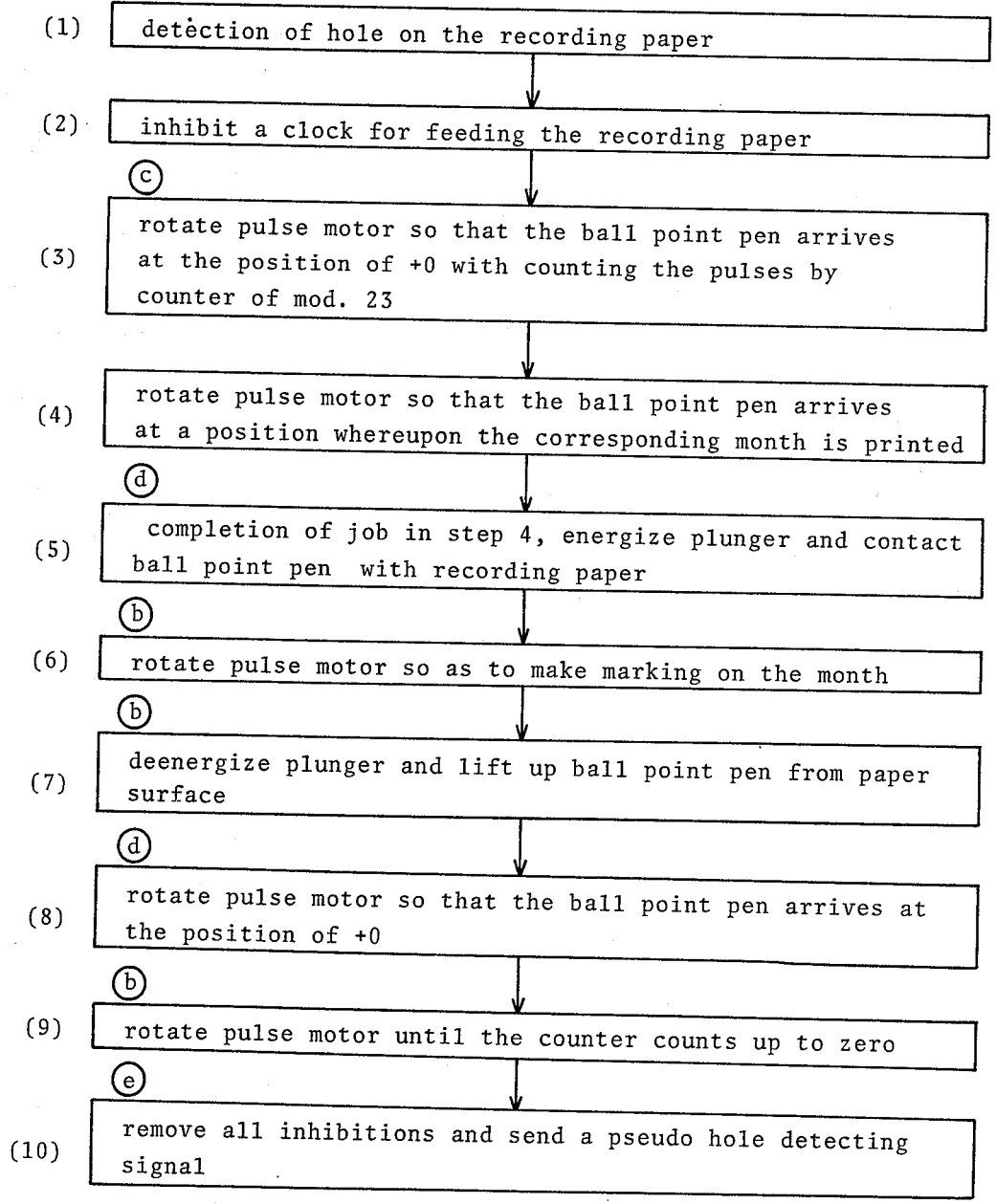

Fig. 12

| Step | |
|---|---|
| (1) | detection of hole on the recording paper |
| (2) | inhibit a clock for feeding the recording paper |
| (3) | rotate pulse motor so that the ball point pen arrives at the position of +0 with counting the pulses by counter of mod. 23 |
| (4) | rotate pulse motor so that the ball point pen arrives at a position whereupon the corresponding month is printed |
| (5) | completion of job in step 4, energize plunger and contact ball point pen with recording paper |
| (6) | rotate pulse motor so as to make marking on the month |
| (7) | deenergize plunger and lift up ball point pen from paper surface |
| (8) | rotate pulse motor so that the ball point pen arrives at the position of +0 |
| (9) | rotate pulse motor until the counter counts up to zero |
| (10) | remove all inhibitions and send a pseudo hole detecting signal |

BIORHYTHM CHART DRAWING-UP APPARATUS

BACKGROUND OF THE INVENTION

This invention relates to a biorhythm chart drawing-up apparatus and particularly to a biorhythm chart drawing-up apparatus which puts out and records monthly a physical rhythm P for a period of 23 days, a rhythm of sentiment (S) for a period of 28 days and a rhythm of intellect (I) for a period of 33 days for an examinee.

We can state that the British Pat. No. 1,430,670 is a prior art of this invention. In this patent, guide numbers of the three rhythms are obtained as the quotient by dividing the number of days of an examinee by the number of days of the rhythms, the starting position of the rhythms of a specified date (hereinafter referred to as a date for examination) can be determined depending on the guide numbers on the respective rhythms. The biorhythm chart drawing-up apparatus for recording a continuous biorhythm is provided with three gears respectively having $n$ times the number of teeth of the numbers of periods of the three biorhythms and means for converting a circular motion into a simple harmonic motion by utilizing a crank and shaft for recording the simple harmonic motions on a recording paper, setting each gear at the starting point for rotating the gear up to the quotient number timed by $n$ and rotating the gears to the $n$ tooth thereof per 1 day and feeding the recording paper for a length of the 1 day, thereby the biorhythm chart for 1 day is drawn up on the recording paper as a part of a sine wave.

To repeat the motion mentioned above, the biorhythms of continuous days are drawn up on the recording paper.

British Pat. No. 1,430,670 discloses a biorhythm calculator which was designed to provide three gears (hereinafter referred to as the first gears) having the same number of teeth on one driving shaft of a motor and three gears (hereinafter referred to as the second gears) having a number of teeth corresponding to the periods of each biorhythm.

The second gears must rotate by the quotient number which is obtained by dividing the number of days from the birthday of the examinee to the day of examination by the number of periods of each biorhythm. To set the second gears at the starting position, this British Patent utilizes a clutch for disengaging the second gears from the first gears and then, solenoids for driving the second gears to set them at their starting position from the zero position and thereafter, the first and second gears become engaged and finally, the three biorhythm charts are drawn up on the recording paper by driving a motor and feeding the recording paper.

Thus, this British patent has a disadvantage in its complicated mechanism. In British Pat. No. 1,430,670, three gears are connected to the one driving shaft and three ball point pens are arranged in a line in a manner of crossing the feeding direction of the recording paper. Consequently, it is impossible to draw up the three biorhythm charts on the single zero line of the recording paper so as to overlap one biorhythm chart upon the other charts.

When current is applied, a ball point pen is forced down onto the recording paper by a magnet against the force of a spring raising the ball pen. Contact pressure of the pen against the recording paper is determined by magnetic attraction of the magnet and a spring force raising the ball pen. Consequently, there is a disadvantage in that the contact pressure of the pen cannot be regulated.

SUMMARY OF THE INVENTION

The object of the present invention is to provide a biorhythm chart drawing-up apparatus which makes the use of gears, clutches and stepping solenoids unnecessary thereby simplifying the mechanism of the present invention.

Another object of the present invention is to provide a biorhythm chart drawing-up apparatus which draws up three biorhythm charts on the same zero line overlapping each chart upon the other.

A further object of the present invention is to provide a biorhythm chart drawing-up apparatus having a recording means which is capable of adjusting the contact pressure of the ball point pens contacting the recording paper.

These and other objects of the present invention will become more fully apparent from the following description of the preferred embodiments with reference to the accompanying drawings.

BRIEF DESCRIPTION OF THE DRAWINGS

FIG. 6-1 to FIG. 6-4 are explanatory flow charts showing the operations of the control unit;

FIGS. 7-1 to 7-6 are connected;

FIGS. 7-1 to 7-6 are block diagrams showing an embodiment of the control unit;

FIG. 8 is a plan of a drawn-up recording paper by another embodiment (hereinafter referred to as the marking embodiment) of the present invention;

FIGS. 9-A to 9-D are block diagrams showing modified block diagrams for embodying the marking embodiment;

FIG. 11 is a timing chart showing timings utilized in FIG. 10;

FIG. 12 is an explanatory flow chart showing operation of the marking embodiment; and FIG. 13 is a partially enlarged view showing a marked portion by the marking embodiment.

PREFERRED EMBODIMENTS OF THE INVENTION

Figure 1:
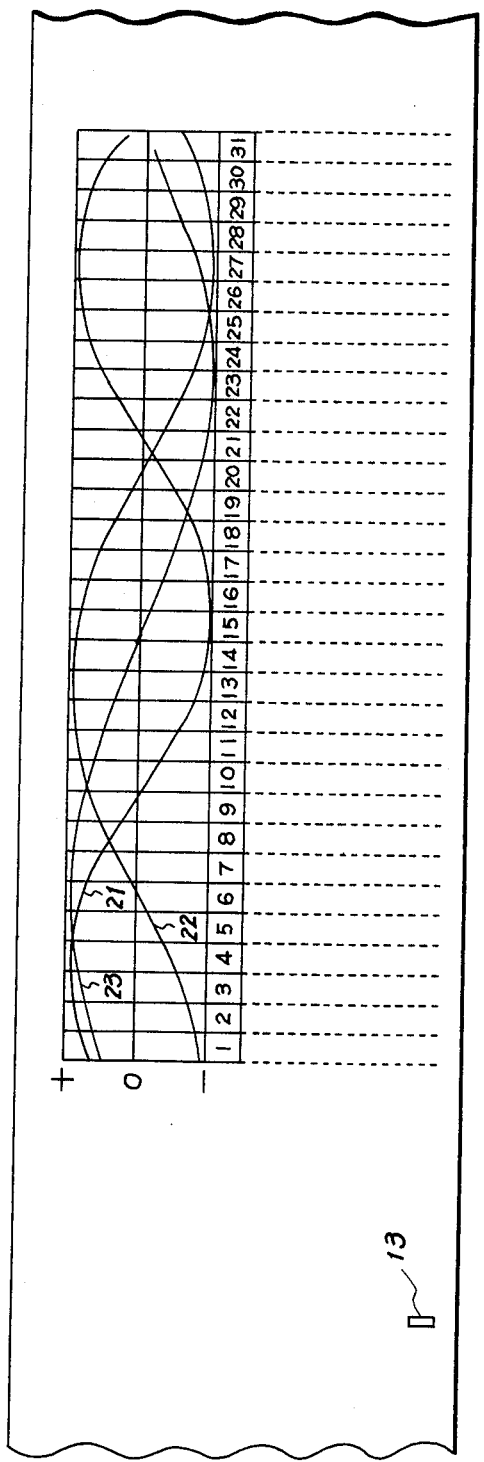
FIG. 1 is one example of a chart drawn up according to the present invention.

FIG. 1 is a plan view showing three biorhythm charts which are drawn up by the apparatus for putting out and recording a biorhythm chart in accordance with the present invention. In FIG. 1, reference numeral 21 represents a physical rhythm (P) having a period of 23 days, reference numeral 22 represents a rhythm of sentiment (S) having a period of 28 days and reference number 23 represents a rhythm of intellect (I) having a period of 33 days. The reference numeral 13 represents a hole. Detection of the hole 13 by a photoconductive sensor 20 initiates the drawing up of the physical rhythm (P) with a ball point pen.

In the drawing, respective active periods are in a domain of "+" belonging to the upper area above the line "O" and inactive periods are in a domain of "−" belonging to the lower area below the line "O."

Figure 2:
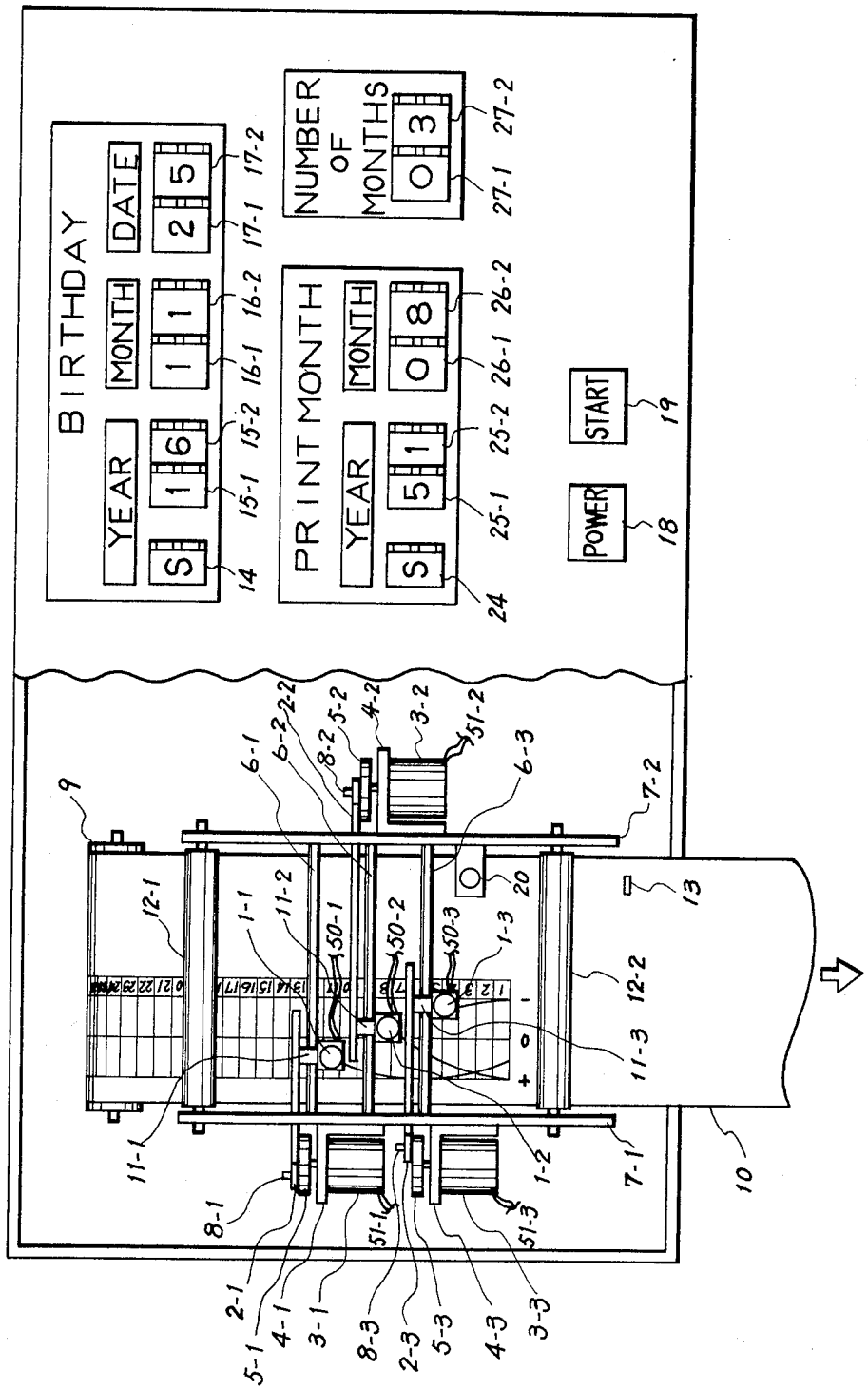
FIG. 2 is a plan view of the apparatus according to the present invention.

In FIG. 2, reference numerals 1-1, 1-2 and 1-3 represent plungers having a ball point pen (hereinafter referred to as a ball pen plunger) for drawing up respective biorhythm charts on the recording paper, in which ball pen plunger 1-1 is utilized for drawing up the physical rhythm (P), ball pen plunger 1-2 is utilized for drawing up the rhythm of sentiment (S) and ball pen plunger 1-3 is utilized for drawing up the rhythm of intellect (I).

The reference numerals 2-1, 2-2 and 2-3 represent piston rods which function to convert a circular motion into a simple harmonic motion. Reference numerals 3-1, 3-2 and 3-3 represent pulse motors which are clamped to the housing plates 7-1 or 7-2 by clamps 4-1, 4-2 and 4-3. Reference numerals 5-1, 5-2 and 5-3 represent discs which are coupled to the output axes of pulse motors 3-1, 3-2 and 3-3 and convert the circular motion into simple harmonic motion.

Reference numerals 6-1, 6-2 and 6-3 represent guide bars which function to guide a linear motion of the ball pen plungers 1-1, 1-2 and 1-3 and are bridged between housing plates 7-1 and 7-2.

The facing angle of the guide bars 6-1, 6-2 and 6-3 to the recording paper is maintained at right angles by housing plates 7-1 and 7-2. Reference numerals 8-1, 8-2 and 8-3 are pins eccentrically extending from the discs 5-1, 5-2 and 5-3 and these pins 8-1, 8-2 and 8-3 cooperate with piston rods 2-1, 2-2 and 2-3 and discs 5-1, 5-2 and 5-3 so as to convert the circular motion of the discs 5-1, 5-2 and 5-3 into simple harmonic motion.

Figure 3:
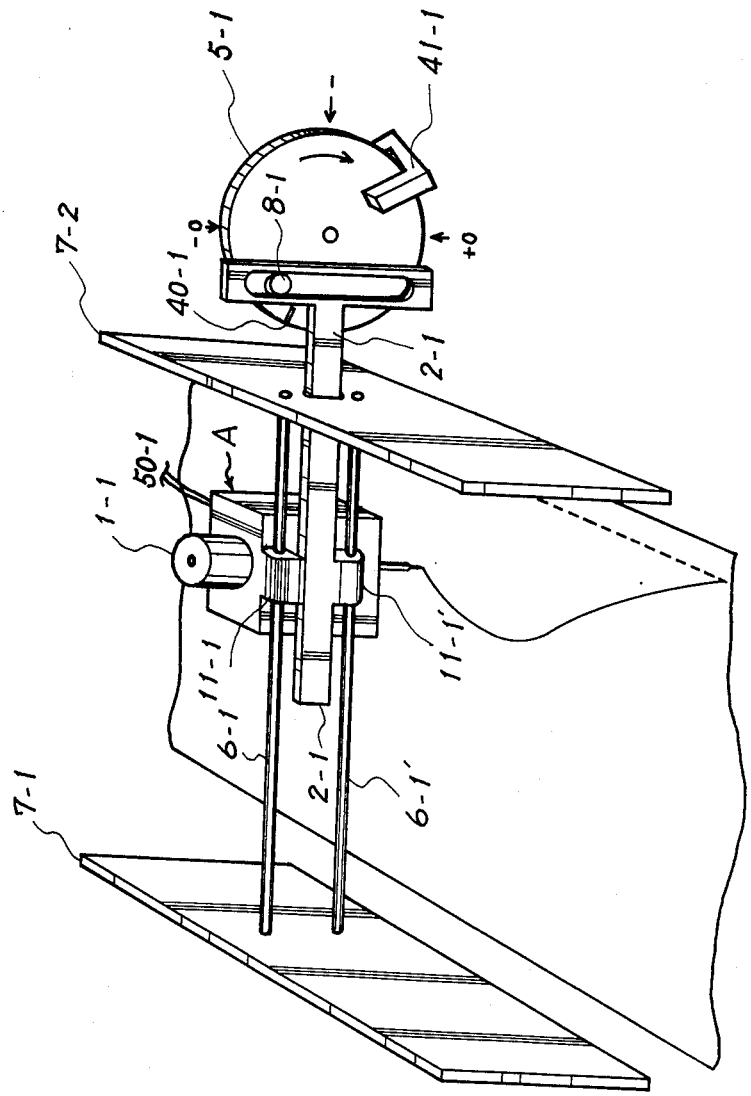
FIG. 3 is a partially enlarged explanatory view taken from FIG. 2.

In FIG. 3, the reference numeral 40-1 represents a slit which is cut away from the disc 5-1 for detecting the position of +0 by the photoconductive cell 41-1. The other slits 40-2 and 40-3 and the other photoconductive cells 41-2 and 41-3 are respectively provided on the discs 5-2 and 5-3 in the same manner. These detection means are customarily used in electronic fields and therefore, same have been left out of the drawings.

Reference numeral 9 represents a roll of a sheet of recording paper 10. Reference numerals 11-1, 11-2 and 11-3 represent guides which are integrally formed with piston rods 2-1, 2-2 and 2-3 and are fixed to ball pen plungers 1-1, 1-2 and 1-3. Guide bars 6-1, 6-2 and 6-3 are guided through guides 11-1, 11-2 and 11-3 so as to move the ball pen plungers in accordance with the simple harmonic motion. Reference numerals 12-1 and 12-2 represent pinch rollers which feed the recording paper 10 in the direction shown by the arrow.

Reference numerals 14, 15-1, 15-2, 16-1, 16-2, 17-1 and 17-2 represent digital switches for setting the birthday of an examinee, in which the reference numerals 14, 15-1 and 15-2 represent digital switches for setting the birthday year. In FIG. 2, reference numeral 14 indicates the name of an era and reference numerals 15-1 and 15-2 indicate the year of the era specified by the reference numeral 14. In the drawings, the abbreviation of M stands for the Meiji Era, T is for the Taisho Era and S is for the Showa Era. It is possible to set the year for the Christian Eras in lieu of Japanese Eras by providing four digit digital switches.

Reference numerals 24, 25-1, 25-2, 26-1 and 26-2 indicate digital switches for setting the date of the biorhythm examination, in which digital switch 24 sets the era in the same manner as digital switch 14 and digital switches 25-1 and 25-2 set the year of the era specified by the digital switch 24. It is possible to set the year of Christian Eras through digital switches in lieu of Japanese Eras by utilizing a four digit digital switch. Reference numerals 27-1 and 27-2 represent digital switches for setting a number of months, counted from the first month, to be recorded.

Reference numeral 18 represents a switch for an electric power source. Reference numeral 19 represents a starting switch for initiating operation of the present invention.

Reference numeral 20 represents a photoconductive cell which detects the hole 13 perforated in the recording paper 10. The hole 13 can be replaced by a mark printed on the recording paper 10. In this case, it is necessary to utilize a mark recognition device instead of photoconductive cell 20.

Reference numerals 50-1, 50-2 and 50-3 represent input signals which activate ball pen plungers 1-1, 1-2 and 1-3, respectively. Reference numerals 51-1, 51-2 and 51-3 represent input signals which activate pulse motors 3-1, 3-2 and 3-3.

We now will describe how to draw up a chart for physical rhythm (P) with reference to FIG. 3.

The operation of the apparatus shown in FIG. 3 can be summarized as follows:

When an input signal is applied to ball pen plunger 1-1, the ball pen plunger 1-1 is forced out from the solenoid A and the tip of the ball pen 60 contacts the surface of the recording paper 10 which is being fed. The biorhythm chart of physical rhythm is drawn up by the cooperating contact of the ball point pen 60 and the running of the recording paper 10. Now, let us presume that disc 5-1 is rotated in the direction of the arrow by the pulse motor 3-1. Pin 8-1, for power transmission, eccentrically extending from disc 5-1, is set into the guide opening 30 provided in the piston rod 2-1 and piston rod 2-1, as detailedly shown in FIG. 3, is integrally molded to form upper and lower slide guides 11-1 and 11-1' at its near end and then, slide guides 11-1 and 11-1' are slidably guided by parallel guide bars 6-1 and 6-1'. Accordingly, the circular motion of disc 5-1 can be converted into simple harmonic motion (reciprocation) of the piston rod 2-1 in cooperation with pin 8-1 and guide opening 30 of piston rod 2-1. Slide guides 11-1 and 11-1' are integrally fixed to form a flange of a solenoid provided with a coil and ball pen plunger 1-1.

When pin 8-1 reaches the maximum minus "−" position, v.z. left end in FIG. 3, ball pen plunger 1-1 moves to the maximum right end of the recording paper 10 as shown in FIG. 3. In other words, ball pen plunger 1-1 moves to the maximum area of plus "+" in FIG. 1. Also, when pin 8-1 moves to the left end (hereinafter this position is referred to as position "+"), ball pen plunger 1-1 moves to the left end of the recording paper 10 as shown in FIG. 3. In other words, pin 8-1 is swung up to the maximum area of "−" in FIG. 1. When pin 8-1 is swung up to the upper end of disc 5-1, the sine wave drawn up by the ball pen, crosses the line "0" from the ascending of "+" to the descending of "−" in FIG. 1. Then, disc 5-1 rotates in the direction of the arrow and pin 8-1 arrives at the lower area and the sine wave crosses the line "0" from descending "−" to ascending "+" as shown in FIG. 3. Thus, the sine wave will be drawn up on the recording paper 10 in cooperation with the rotation of disc 5-1 at a fixed speed and feeding of the recording paper 10 at a fixed speed. Accordingly, by controlling the speed of rotation of disc 5-1 so as to correspond with the feeding speed of recording paper 10, physical rhythm (P) with a period of 23 days can be drawn up on the recording paper 10 corresponding to days pre-printed on the recording paper 10. In the same manner, the sine wave for rhythm of sentiment (S) with a period of 28 days and the sine wave for rhythm of intellect (I) with a period of 33 days can also be drawn up on the recording paper 10.

Next, the construction of the ball pen plunger will be described with reference to FIG. 4.

Reference numeral 61 indicates a coil. When a current is applied to the coil 61, a ferrite core 62 is pulled out and downward. Prior to the ferrite core 62 being pulled out, it is lifted by a spring wound around a baseplate 63 and a pen guide 65 is thus thrust into ferrite core 62 and ball pen 60 is also lifted upward and ball pen 60 maintains the non-contacting position from the surface of the recording paper 10. However, when the ferrite core 62 is pulled out, ball pen 60 contacts the recording paper 10 and is ready to draw up the rhythm chart.

Figure 4:
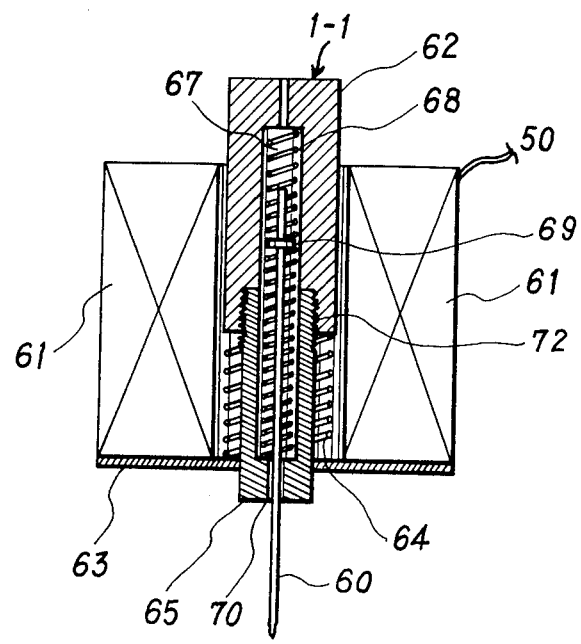
FIG. 4 is a vertical sectional view of a ball point pen holder for illustrating the construction thereof.

As shown in FIG. 4, ferrite core 62 and pen guide 65 are tubular and by thrusting the pen guide 65 into ferrite core 62, enclosing spaces provided in the interior of pen guide 65 and ferrite core 62 are communicated so as to form one enclosing space 67 wherein coil spring 68 is enclosed.

Ball pen 60 is provided with a collar at its near end with its diameter being nearly equal to the inside diameter of the enclosing space 67 so as to be able to move upward and downward in the enclosing space 67 and the top end of the ball pen 60 is pushed out in a direction of the recording paper 10 through a hole 70 and extends past the pen guide 65. The coil spring 68, enclosed in the enclosing space 67, is divided into an upper part and a lower part.

When the ball pen 60 is forced upward by the recording paper 10 during recording, the lower part of spring 68 is expanded and the upper part of spring 68 is depressed. On the contrary, when the contact pressure applied to the ball point pen 60 by recording paper 10 is weakened by the wavy motion of the recording paper 10, the upper part of spring 68 is expanded and the lower part of spring 68 is depressed. In this manner, the contact pressure of ball pen 60 upon the recording paper 10 can be adjusted to afford a desirable contact pressure by utilizing elasticity of the coil spring 68.

A male screw is provided on the thrusting portion of the pen guide 65 and a threaded portion is provided on the inner surface of the ferrite core 62 and thus, the pen guide 65 is screwed into the ferrite core 62 up to the desirable depth so as to determine the length of enclosing space 67. Thus, by adjusting the screw portion 72, it serves to modify the contact pressure.

An operation of the apparatus according to the present invention is controlled by a control unit 100. The operation of this invention utilizing the control unit 100 will now be detailedly described. It will be easily understood that the control unit 100 may be embodied by utilizing one-tip CPU or logic circuits.

FIGS. 6-1, 6-2, 6-3 and 6-4 show flow charts which are described in connection with control unit 100.

Figures 4, 6:
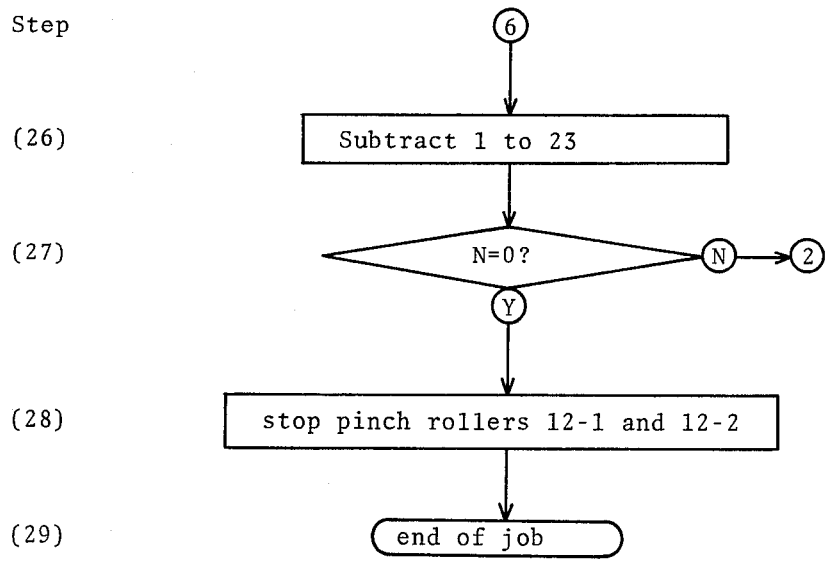
Figure 5:
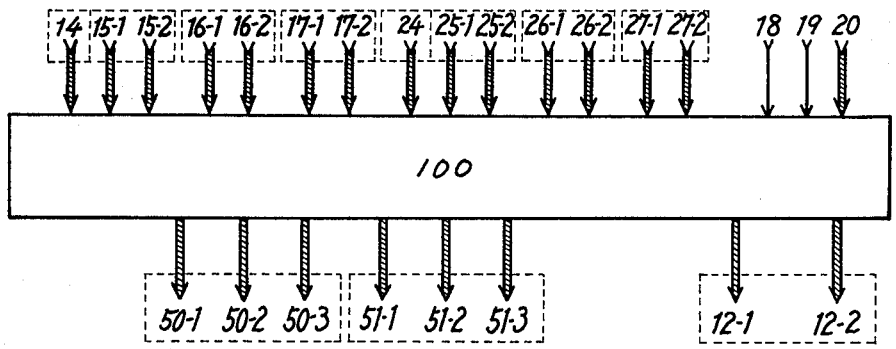
FIG. 5 is an explanatory view illustrating the relations between the control unit and signals.
Figures 1, 6:
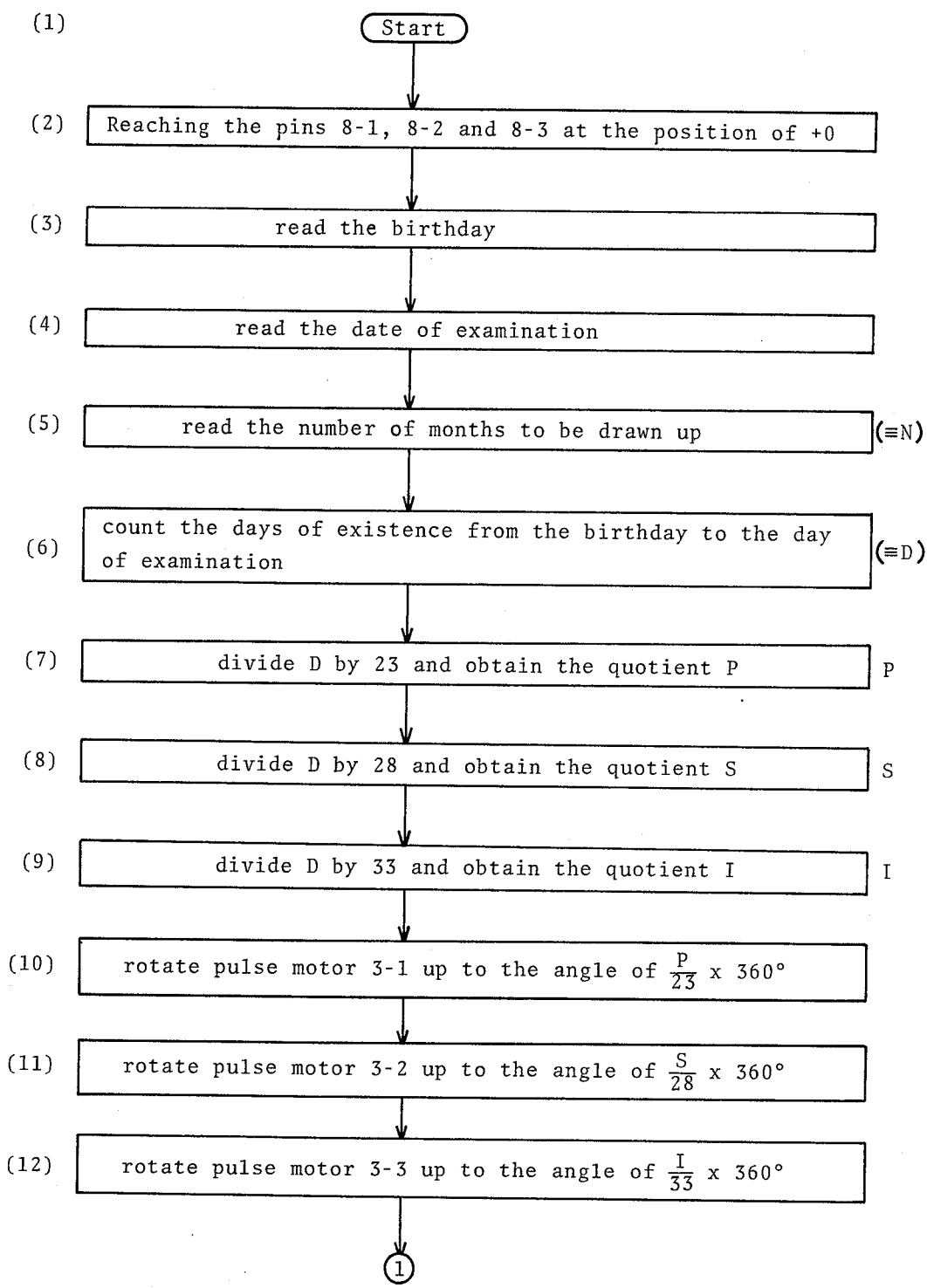
Figures 3, 6:
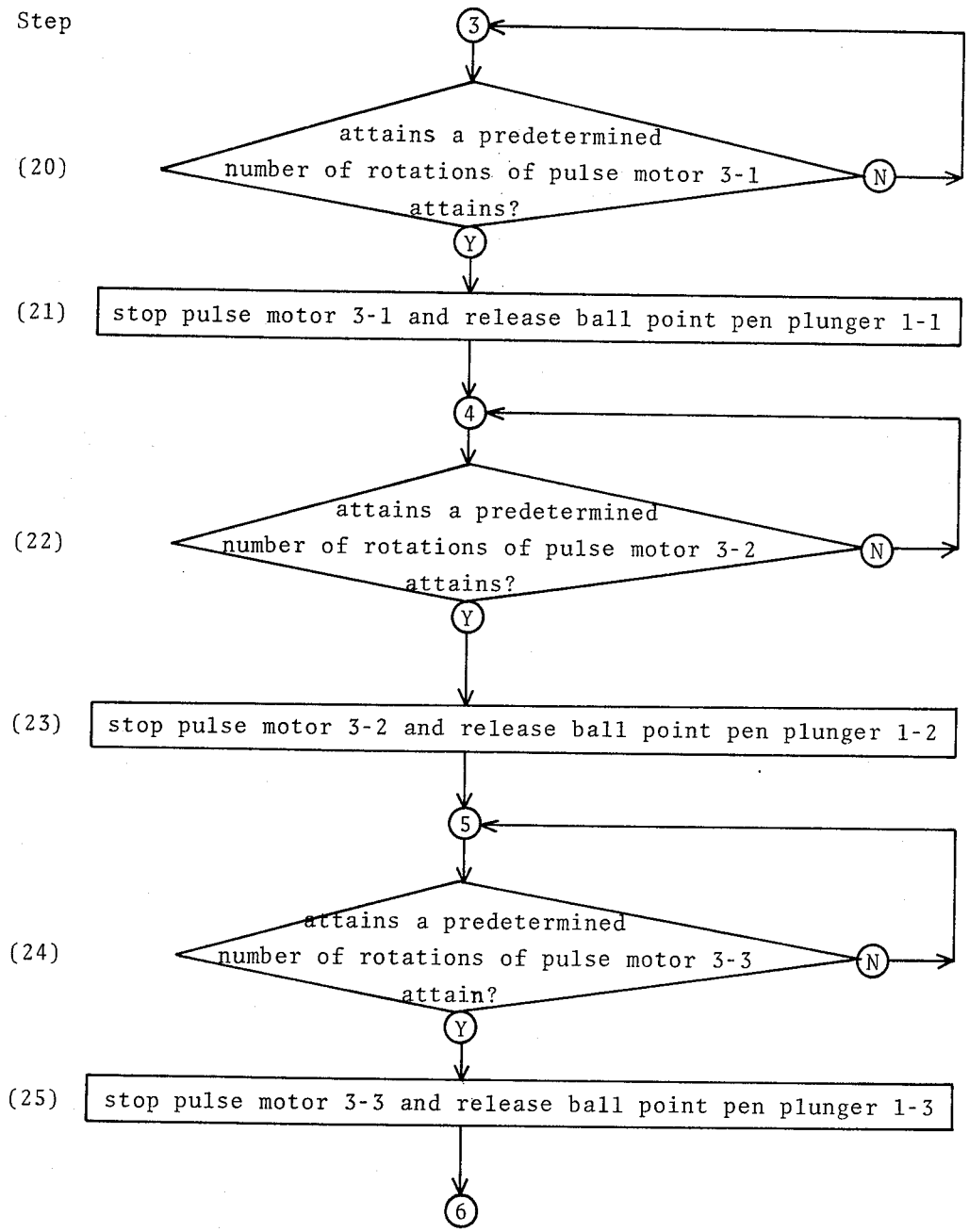
Figures 1, 7:
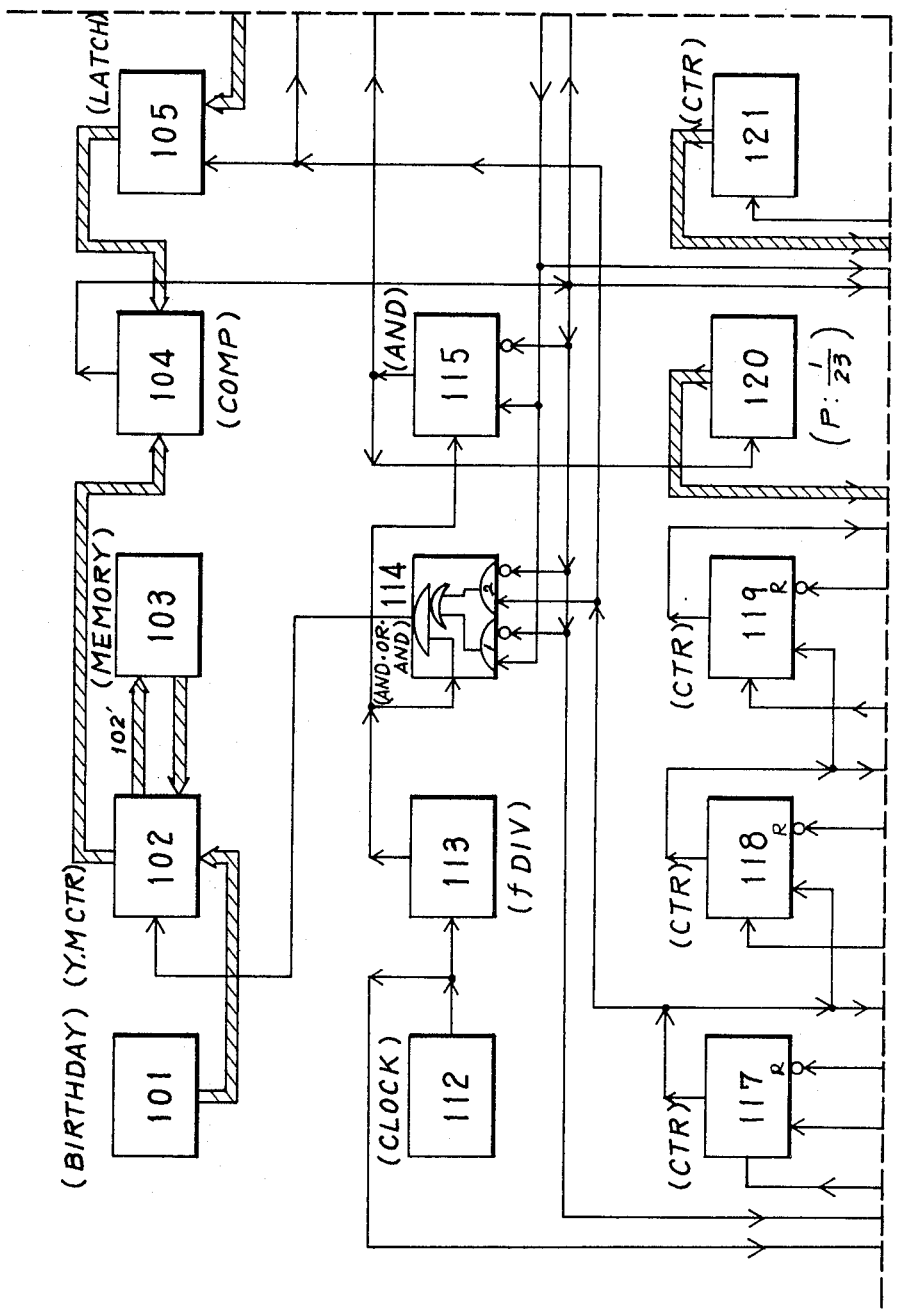
Figures 2, 7:
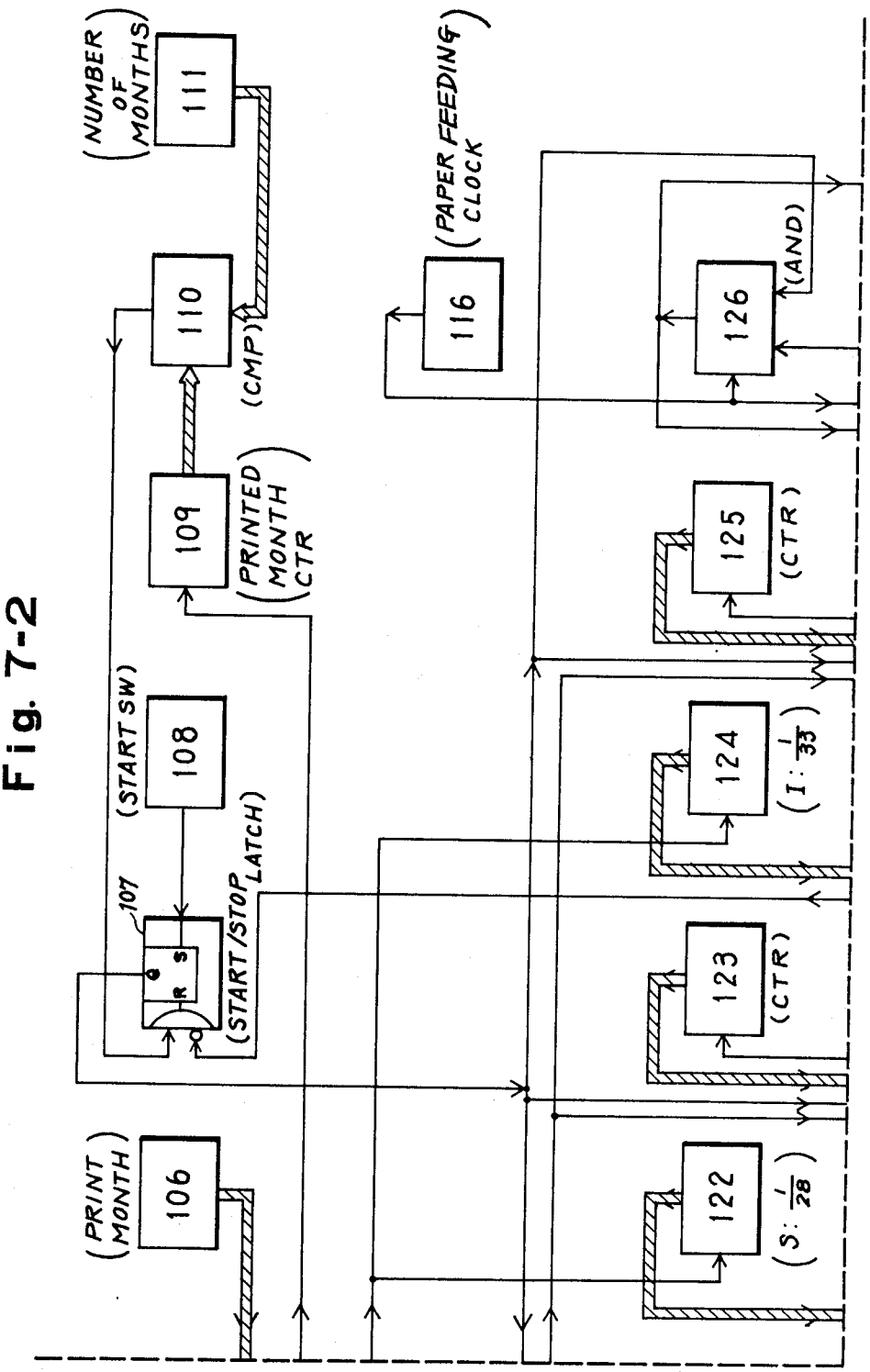
Figures 3, 7:
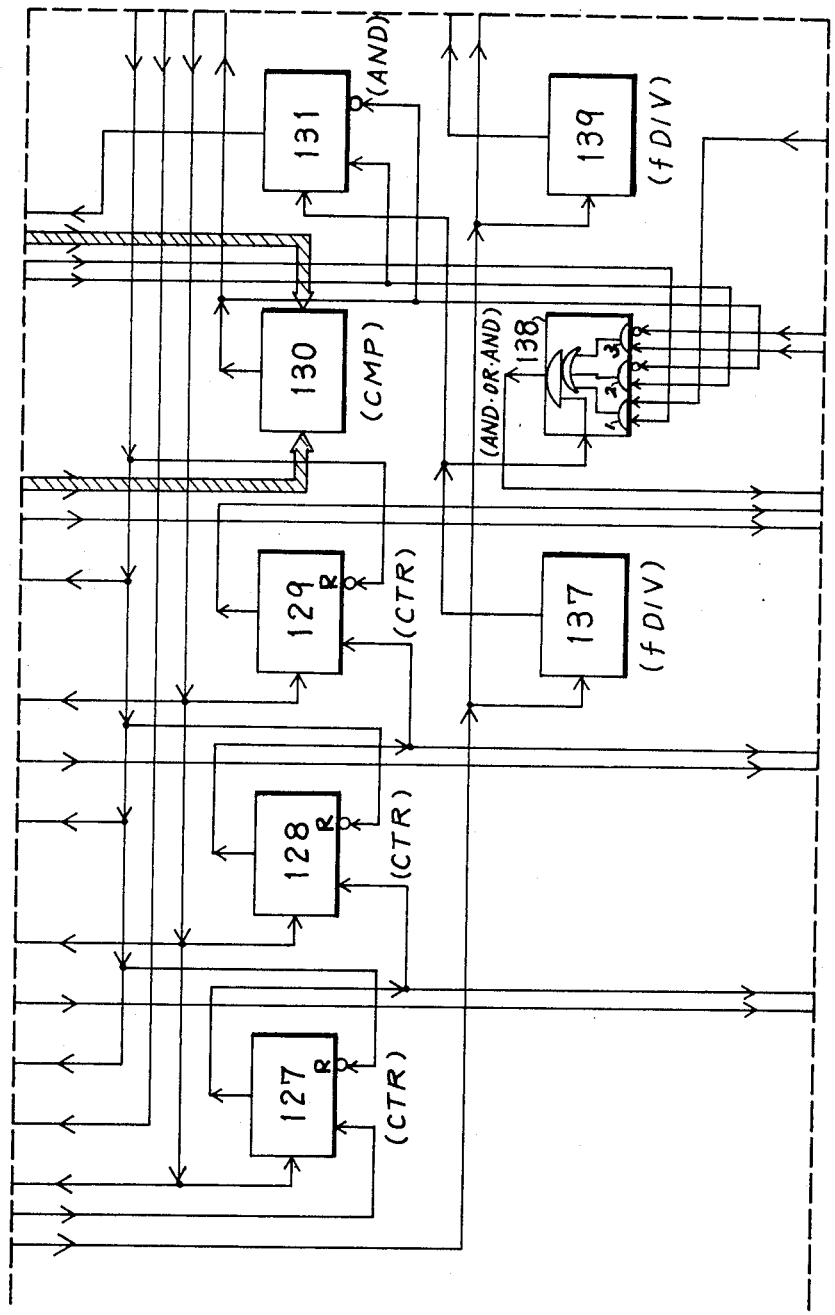
Figures 4, 7:
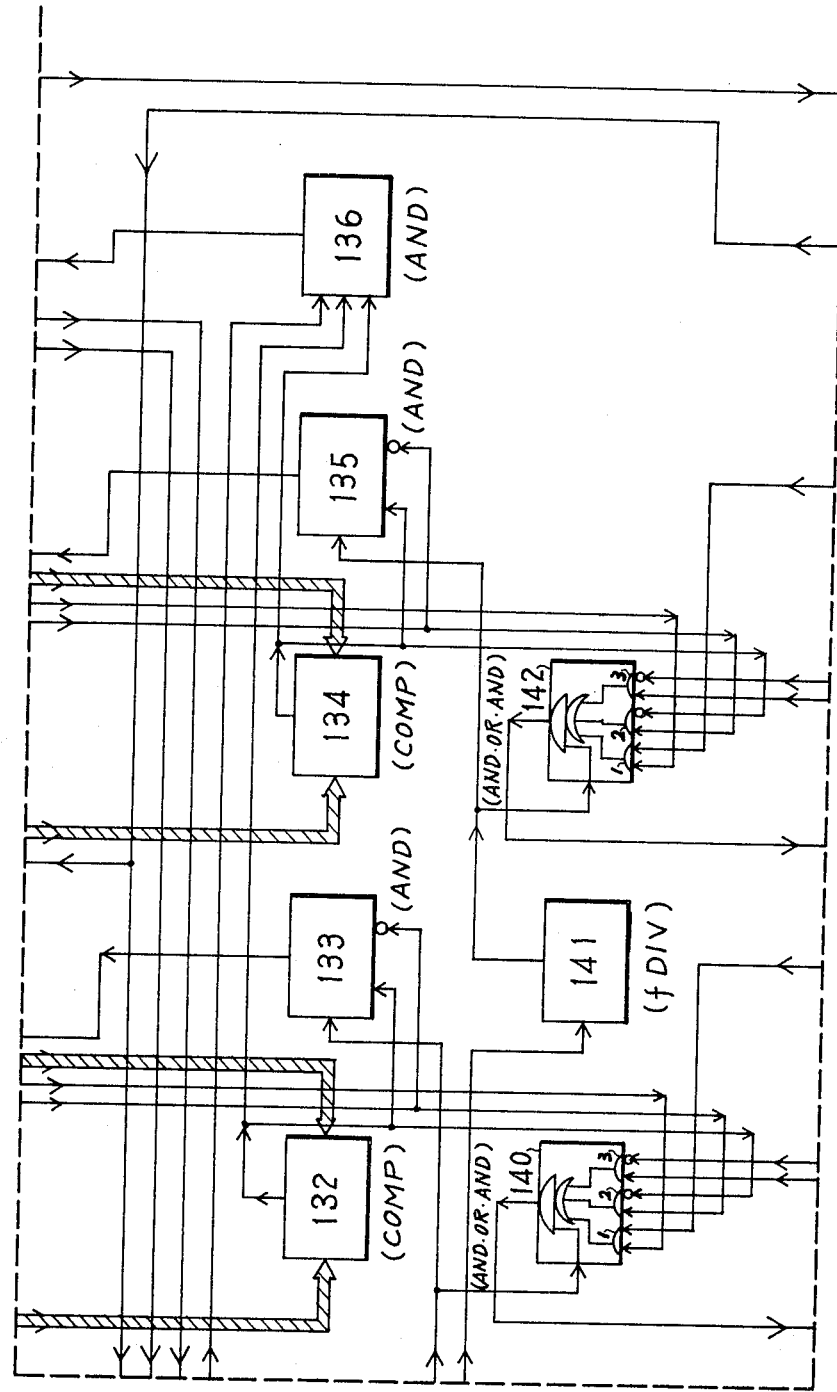

Firstly, the operator of the apparatus applies the electric source and then he puts in the birthday of the examinee, the day of examination and the number of months to be recorded and finally, he pushes a starting switch 19. Thus, step 1 in FIG. 6-1 is completed.

Then, control unit 100 advances the control to step 2, signals 50-1, 50-2 and 50-3 are sent out to move the pins 8-1, 8-2 and 8-3 to the position marked as +0.

Next, step 2 advances to step 3, control unit 100 reads the birthday and step 3 advances to step 4, control unit 100 reads the date of examination and step 4 advances to step 5. At step 5, the number of months (N) to be drawn up are read by the control unit 100 and then step 5 advances to step 6. At step 6, the days of existence from the birthday to the day of examination is calculated. The days of existence are defined as D. Then step 6 advances to step 7. At step 7, D is divided by 23 and the quotient P is obtained therefrom and step 7 advances to step 8. At step 8, D is divided by 28 and quotient S is obtained therefrom and step 8 advances to step 9. At step 9, D is divided by 33 and quotient I is obtained therefrom.

Accordingly, the present invention is so designed, that one rotation of pulse motor 3-1 is obtained by supplying 23 pulses and by supplying a number of pulses corresponding to the quotient P, the rotation angle of pulse motor 3-1 is progressed per P from the position of +0. In other words, to perform the above-mentioned operation, the pulse motor 3-1 is rotated and the angle calculated by dividing the quotient P by 23 and multiplying by 360°, that is, ((P/23) × 360°).

In the same manner, at step 11, S is divided by 28 and the pulse motor 3-2 is rotated up to the angle of (S/28) × 360° and at step 12, I is divided by 33 and the pulse motor 3-3 is rotated up to the angle of I/33 × 360°.

Upon completion of the above-mentioned operations, ball pens are positioned at their respective starting points and are ready to draw up the charts.

Proceedings advance to the steps connected to connector 1 shown in FIG. 6-2. In step 13, the control unit 100 controls pinch rollers 12-1 and 12-2 so as to feed the recording paper 10. In step 14, detection of the hole 13 by the photoconductive cell 20 is carried out. This step is continued until the hole is detected. If the photoconductive cell 20 cannot detect the hole 13, the step is backed up to the connector 2. When the hole 13 is detected, the control is advanced to step 15. In step 15, pulse motor 3-1 is rotated to complete one rotation with 23 pulses and at the same time, ball pen plunger 1-1 is pulled out for drawing up the chart.

As is apparent in FIG. 2, after a time T1, the starting position for drawing up the rhythm of sentiment (S) on the recording paper 10 arrives under the ball pen plunger 1-2. This time lag for T1 is generated in step 16. When the starting point arrives at the ball pen plunger 1-2, the step 16 advances to step 17 and the pulse motor 3-2 is rotated with a period of 28 days under the control of control unit 100.

Simultaneously, ball pen plunger 1-2 is pulled out and starts to draw up the rhythm of sentiment (S) on the recording paper 10.

After the time lapse T2, the starting point (this starting point being on the same position as the starting point for the physical rhythm (P) and the rhythm of sentiment (S)) arrives under the ball pen plunger 1-3. This time lapse T2 is generated in step 18. When the starting point arrives at the ball pen plunger 1-3, step 18 advances to step 19 and the pulse motor 3-3 is rotated with a period of 33 days under the control of control unit 100. Simultaneously, ball pen plunger 1-3 is pulled out and starts to draw up the chart for the rhythm of intellect (I).

The control step 19 advances to the subsequent steps after connector 3 as shown in FIG. 3.

In step 20, determination as to whether or not the number of rotations of pulse motor 3-1 reaches the predetermined number of rotations, is carried out. In the case where the number of rotations are less than the predetermined value, the step returns to connector 3 and the same step is continued. When the number of rotations of the pulse motor 3-1 attains the predetermined value, the step 20 advances to step 21 and pulse motor 3-1 is stopped in its rotation and further, ball pen plunger 1-1 is released so as to remove the ball pen from the recording paper 10. Then, step 21 advances to step 22.

In step 22, determination as to whether or not the number of rotations of pulse motor 3-2 reaches the predetermined number of rotations is carried out. In the case where the number of rotations are less than the predetermined value, the step returns to connector 4 and the same step 22 is continued. When the number of rotations of the pulse motor 3-2 attains the predetermined value, the step 22 advances to step 23 and pulse motor 3-2 is stopped in its rotation and further, ball pen plunger 1-2 is released so as to remove the ball pen from the recording paper 10. Thereafter, step 23 advances to step 24.

In step 24, determination as to whether or not the number of rotations of pulse motor 3-3 reaches the predetermined number of rotations is carried out. In case the number of rotations are less than the predetermined value, the step 24 returns to connector 5 and the same step 24 is continued. When the number of rotations of the pulse motor 3-3 attains the predetermined value, the step 24 advances to step 25 and pulse motor 3-3 is stopped in its rotation and further, ball pen plunger 1-3 is released so as to remove the ball pen from the recording paper 10.

The control procedure advances to the steps mentioned in FIG. 6-4, which is connected to the connector 6. In step 23, the number N, being read by the control unit 100, substracts one "1" and the result thereof is replaced by a new value N. The step 23 advances to step 24 and the determination as to the fact that N is equal to zero is carried out. When N is not zero, the control procedure returns to connector 2 in FIG. 6-2 and the steps after step 14 are carried out. When N is zero in step 24, the step 24 advances to step 25 and rotation of pinch-rollers 12-1 and 12-2 are stopped. Thereafter, step 25 advances to step 26 and all action is completed.

A hard-wired-logic which is embodied in the control unit 100 will hereinafter be explained.

Figure 7:
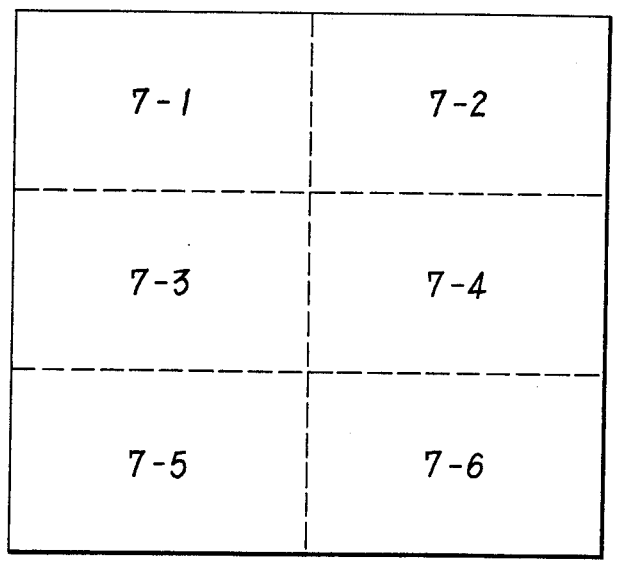
FIG. 7 is an explanatory view showing how

The hard-wired-logic is shown in FIG. 7-1 to FIG. 7-6 and the explanation is performed in the sequence of the operation.

(a) At the first operation, the birthday of the examinee is set by the digital switch 101 (this digital switch 101 includes the digital switches 14, 15-1, 15-2, 16-1, 16-2, 17-1 and 17-2 in FIG. 2).

(b) Then, the date of examination is set by digital switch 106 (this digital switch 106 includes digital switches 24, 25-1, 25-2, 26-1 and 26-2 in FIG. 2).

(c) Next, the number of months to be recorded on the biorhythm chart is set by digital switch 111 (this digital switch 111 includes digital switches 27-1 and 27-2 in FIG. 2).

(d) Starting switch 108 (this switch 108 corresponds to the starting switch 19 in FIG. 2) is pushed after all the operations mentioned above are completed. Thus, start/stop latch circuit 107 is set.

(e) the number in counter 109 which counts the number of recorded months is zero at the first stage and thus, the inverted output of a comparator 110 is a truth signal and the start/stop latch circuit 107 puts out the truth signal.

At this time, if an output of comparator 104 is a false signal, an AND circuit 1 of logic 114 and AND circuit 15 is enabled.

An output of clock generator 112 is desirably divided by frequency divider 113 and then supplied to the above-mentioned AND circuit 1 of logic circuit 114 and AND circuit 115, respectively.

Then, and output of logic circuit 114 is counted by counter 102 for counting the year and month and an output of AND circuit 115 is counted by P counter 120 (a scale of 1/23 counter), S counter 122 (a scale of 1/28 counter), I counter 124 (a scale of 1/33 counter). In this calculation, 1 pulse is treated as 1 day.

In order to compensate for different numbers of days in different months and for the effects of leap years, the counter 102 is automatically adjusted to 28, 29, 30 and 31 days by referring to a memory circuit 103 which stores information as to leap years, 31-day months and months with 30 or less days.

An output of the digital switch 106, being set at the date for examination, is latched by a counter latch circuit 105. An output of the counter latch circuit 105 and the output of the counter 102 are compared by comparator 104. When a coincidence of those two outputs from the counter 102 and counter latch circuit 105 is obtained, the comparator 104 puts out a signal of truth. The output of the comparator 104 disables the AND circuits of logic circuit 114 and AND circuit 115 from putting out false signals. Thus, the counter 102 stops counting.

The P counter 120 divides the output of AND circuit 115 by 23 and stops the division when the quotient P is obtained. The S counter 122 divides the output of AND circuit 115 by 28 and stops the division when the quotient S is obtained and the I counter 124 divides the output of AND circuit 115 by 33 and stops the division when the quotient I is obtained.

(f) The output of start/stop latch circuit 107 is respectively supplied to AND circuits specified as 1 in logic circuits 138, 140 and 142. The output of clock generator 112 is divided by dividers 137, 139 and 141 with specified dividing rates (the dividing rates will be described hereinafter), and supplied to the circuits 138, 140 and 142. Accordingly, the logic circuits 138, 140 and 142 respectively put out signals in association with the dividers 137, 139 and 141. The output of logic circuit 138 is supplied to a motor driver 146 wherein the output is amplified and supplied to the pulse motor 3-1 via a terminal 157 and a signal line 51-1. Also, the output of logic circuit 140 is supplied to a motor driver 148 wherein the output is amplified and supplied to the pulse motor 3-2 via a terminal 159 and a signal line 51-2. At the same time, the output of logic circuit 142 is supplied to the motor driver 150 wherein the output is amplified and supplied to the pulse motor 3-3 via a terminal 161 and signal line 51-3.

(g) Then, the discs 5-1, 5-2 and 5-3 start to rotate. As seen from FIG. 3, the disc 5-1 rotates and when a slit 40-1 cuts across under the photoconductive cell 41-1, an output signal is obtained from the photoconductive cell 41-1. In the same manner, respective slits and photoconductive cells are provided on respective discs 5-2 and 5-3. The outputs of the respective photoconductive cells are obtained in thus manner and the output corresponding to the disc 5-1 is applied to an input terminal 158, the output for the disc 5-2 is applied to an input terminal 160 and the output for the disc 5-3 is applied to an input terminal 162. Those outputs are inverted by inverting amplifiers 147, 149 and 151 and then respectively applied to AND circuit 1 of the logic circuits 138, 140 and 142. Accordingly, after detection of the slits by the photoconductive cells, the outputs of logic circuits 138, 140 and 142 are inhibited. Each pulse motor stops its rotation due to the fact that there are no outputs from the motor drivers.

As the pins 8-1, 8-2 and 8-3 are previously adjusted to be positioned at the position of $+0$ at the time of detection of the slits 40-1, 40-2 and 40-3 by the photoconductive cells, each pulse motor stops at the position where each pin reaches the position of $+0$. By performing these operations, ball point pens are set at their zero positions.

(h) After positioning each ball point pen at the $+0$ position, by coincidence of two input values of comparator 104, AND circuits 2 of logic circuits 138, 140 and 142 are enabled (the outputs of comparator 130, 132 and 134 are deemed to be false signals). Each output of the frequency dividers 137, 139 and 141 are applied to the motor drivers 146, 148 and 150 through the logic circuits 138, 140 and 142 so as to drive the pulse motors 3-1, 3-2 and 3-3.

The dividing ratios of dividers 137, 139 and 141 are given equations of $1/(28 \times 33) : 1/(23 \times 33) : 1/(23 \times 28)$ under the conditions of "$f$" for frequency of clock generator 112 being defined as $f = 23 \times 28 \times 33 \times N$ ($N$ being a positive integer), and a number of poles of pulse motors 3-1, 3-2 and 3-3 being defined as N.

At the time of being enabled, the AND circuit 2 of logic circuits 138, 140 and 142, AND circuits 131, 133 and 135 are enabled simultaneously.

The ratio of frequency dividing of frequency dividers 137, 139 and 141 are defined so that the outputs of frequency dividers 137, 139 and 141 are supplied with a number of N pulses and these N pulses are then supplied to pulse motors 3-1, 3-2 and 3-3 while the recording paper 10 is fed the distance for 23 days, 28 days and 33 days, respectively. Those outputs of frequency dividers 137, 139 and 141 are counted by counters 121, 123 and 125 and compared with the quotients of a P counter 120, S counter 122 and I counter 124 by comparators 130, 132 and 134. When the coincidence is obtained by this comparison, the comparators 130, 132 and 134 supply truth signals to the logic circuits 138, 140 and 142 and AND circuits 131, 133 and 135 so as to disable those logic circuits 138, 140 and 142 and AND circuits 131, 133 and 135. Accordingly, the pulse motors 3-1, 3-2 and 3-3 rotate up to the angles of $(P/23) \times 360°$, $(S/28) \times 360°$ and $I/33 \times 360°$, prior to disabling and then they are stopped. Thus, the ball point pen plungers 1-1, 1-2 and 1-3 are set at the starting position to draw up the biorhythm charts by the rotations of discs 5-1, 5-2 and 5-3.

(i) In this manner, when a job for setting the ball point pen plungers at the their starting positions is completed, truth outputs are obtained from the comparators 130, 132 and 134 so as to enable an AND circuit 136.

Then, and AND circuit 126 (the other input of the AND circuit is truth) is enabled to supply clocks to a motor driver 153 in synchronization with clocks supplied from a clock generator 116 utilized for recording paper feeding. The input for motor driver 153 is supplied to a motor (not shown in the drawing) for feeding the recording paper 10 through a terminal 164 so as to rotate the pinch rollers 12-1 and 12-2 for feeding the recording paper 10.

(j) The output of clock generator 116 is also supplied to counters 117, 118, 119, 127, 128 and 129 and when the AND circuit 126 is enabled, the counter, at first, starts to count the clock from the clock generator 116. The counter 117 counts up to a predetermined number of pulses which gives a distance for the recording paper 10 to be fed so as to feed and reach the recording position for the first day of a month to be recorded on the paper 10 just under the ball point pen plunger 1-1. The counter 117 puts out a truth signal when the counter counts up the predetermined number of pulses. A plunger driver 143 receives the signal of truth and energizes the ball pen plunger 1-1 through a terminal 154 so as to contact the ball point pen 60 with the recording paper 10 and the ball point pen is now ready to draw up the chart.

(k) The plunger driver 143 is energized and at the same time, and AND circuit 3 of logic circuit 138 is enabled by the motor driver 146 and supplied to the pulse motor 3-1 through the terminal 157. Thus, the pulse motor 3-1 starts its rotation and draws up the charts.

(l) The counter 118 counts the pulses from clock generator 116 after obtaining the output from counter 117 and further counts up to a predetermined number of pulses which gives a distance for the recording paper 10 to be fed so as to feed and reach the recording position for the first day of a month to be recorded on the recording paper 10 just under the ball point pen plunger 1-2. The counter 118 puts out a truth signal when the counter counts up the predetermined number of pulses. A plunger driver 144 is supplied with the output and amplifies same therein and energizes the ball point pen plunger 1-2 through a terminal 159 so as to contact the ball point pen with the recording paper 10. The plunger driver 144 is energized and at the same time, AND circuit 3 of logic circuit 140 is enabled. The output of logic circuit 140 is amplified by the motor driver 148 and then supplied to the pulse motor 3-2 through the terminal 159 and the line of 51-2 so as to rotate the pulse motor 3-2 and to draw up the chart of rhythm of sentiment S on the recording paper 10.

(m) In the above manner, the counter 119 counts the pulses from clock generator 116 after obtaining the output of counter 118 and further counts up to a predetermined number of pulses which gives a distance the recording paper is to be fed so as to feed and reach the recording position for the first day of a month to be recorded on the recording paper 10 just under the ball point pen plunger 1-3. The output of counter 119 is amplified by the plunger driver 145 and energizes the ball point pen plunger 1-3 so as to contact the ball point pen with the recording paper 10. Simultaneously, AND circuit 3 of the logic circuit 142 is enabled and the output of logic circuit 142 is supplied to the motor driver 150 and amplified therein. The output of motor driver 150 is supplied to the pulse motor 3-3 so as to rotate same.

(n) An AND circuit 2 of logic circuit 114 is enabled, when the output of counter 117 is obtained and two inputs of comparator 104 do not coincide, to supply an output coincidence with the output of frequency divider 113 to the counter 102. The counter 102 counts up the pulses supplied from the logic circuit 114. Simultaneously, each 1 (one) pulse (corresponding to 1 month) is counted up in counter latch circuit 105 and a counter 109 for counting the number of recorded months. At the time of completion of counting up for one month, by the coincidence of two inputs of comparator 104, the comparator 104 puts out a truth signal for disabling the AND circuit 2 of logic circuit 114 for stopping output therefrom.

(o) Due to the signal being supplied from the comparator 104, the counter 127 starts to count the pulses. The counter 127 counts up to a predetermined number of pulses which gives a distance for the recording paper 10 to be fed so as to feed and reach the recording position corresponding to the last day of a month on the recording paper 10 just under the ball point pen plunger 1-1. The counter 127 puts out a truth signal when the counter counts up the predetermined number of pulses. Thus, the plunger driver 143 is deenergized by the negative input from the counter 127 and the current applied to the coil 61 is interrupted. Then, the ball point pen 60 is pulled up from the recording paper 10 and at the same time, the AND circuit 3 of logic circuit 138 is disabled and stops its output. The output of motor driver 146 is interrupted and thus, the pulse motor 3-1 stops.

(p) The counters 128 and 129, in sequence, count up to a predetermined number of pulses which rotates the pulse motors in order to feed the recording paper to distances between the ball point pen plungers 1-1 and 1-2 and 1-2 and 1-3, respectively. When the counters 128 and 129 count up the predetermined number of pulses, truth signals are supplied to the plunger drivers 144 and 145. Thus, the current supplied to the coils of ball point pen plungers 1-2 and 1-3 are interrupted, thereby pulling up the ball point pens. At the same time, the outputs of counters 128 and 129 are respectively supplied to the AND circuits 3 of logic circuits 140 and 142, thereby disabling same. Thus, the pulse motors 3-2 and 3-3 are stopped in their rotations.

(q) Feeding of the recording paper 10 is still continued and when the hole 13 reaches the position of photoconductive cell 20, the output of photoconductive cell 20 is supplied to a terminal 163. The input of terminal 163 is supplied to a start-input of start/stop latch circuit 107. At this time, if there is no input from the comparator 110, the start/stop latch 107 is not reset. The output of inverting amplifier 152 resets the counters 117, 118, 119, 127, 128 and 129 and the stage is advanced to draw up the chart of the following month. In other words, the control step is returned to the step of (i) mentioned above and the control step is performed in sequence.

The start/stop latch 107 is reset by enabling reset-input thereof from the truth output comparator 110. Then, the AND circuit 126 is disabled, thereby interrupting the output for recording paper feeding by the motor driver 153. Thus, the recording paper 10 is not fed.

The examinee's biorhythm chart for June, for example, is now drawn up on the recording area of the recording paper 10 as shown in FIG. 8. Accordingly, it is necessary to allow the examinee to specify the month now being drawn up on the chart by marking the corresponding month between a group of months, that is, January to December, which are vertically printed on the left side of the recording paper 10.

Hereinafter, the marking will be discussed.

For embodying this mechanism, FIG. 7 is partly modified into FIG. 9. In modification, a marked "xx" portion indicates a cut out portion and an obliquely lined AND circuit or OR circuit indicates the circuits which are added in order to achieve this embodiment.

As illustrated in FIG. 9A, the output of clock generator 116 for feeding the recording paper 10 and an output $\overline{CF2}$ of JK master-slave flip-flop 202 are anded by an AND circuit 300 and then an output of AND circuit 300 is supplied to the next step. The output of inverting amplifier 147 and the signal $\overline{CF2}$ are anded by an AND circuit 301 and then supplied to the next step. The output of clock generator 112 and the signal $\overline{CF2}$ are anded by an AND circuit 302 and then supplied to the next step.

As illustrated in FIG. 9B, the output of inverting amplifier 152 is supplied to a terminal (a). An output of terminal (e) is supplied to a line from inverting amplifier 152.

As illustrated in FIG. 9C, an amplifying part of plunger driver 143 is supplied an output CF5 of JK master-slave flip-flop 212 through an OR circuit 304.

As illustrated in FIG. 9D, an output of terminal (b) is anded with the output of AND circuit 138 by AND circuit 305 and the logically anded output thereof is supplied to the motor driver 146. The terminals (a) to (e) discussed with reference to the above explanation are respectively connected to the same terminals (a) to (e) in FIG. 10.

Figure 10:
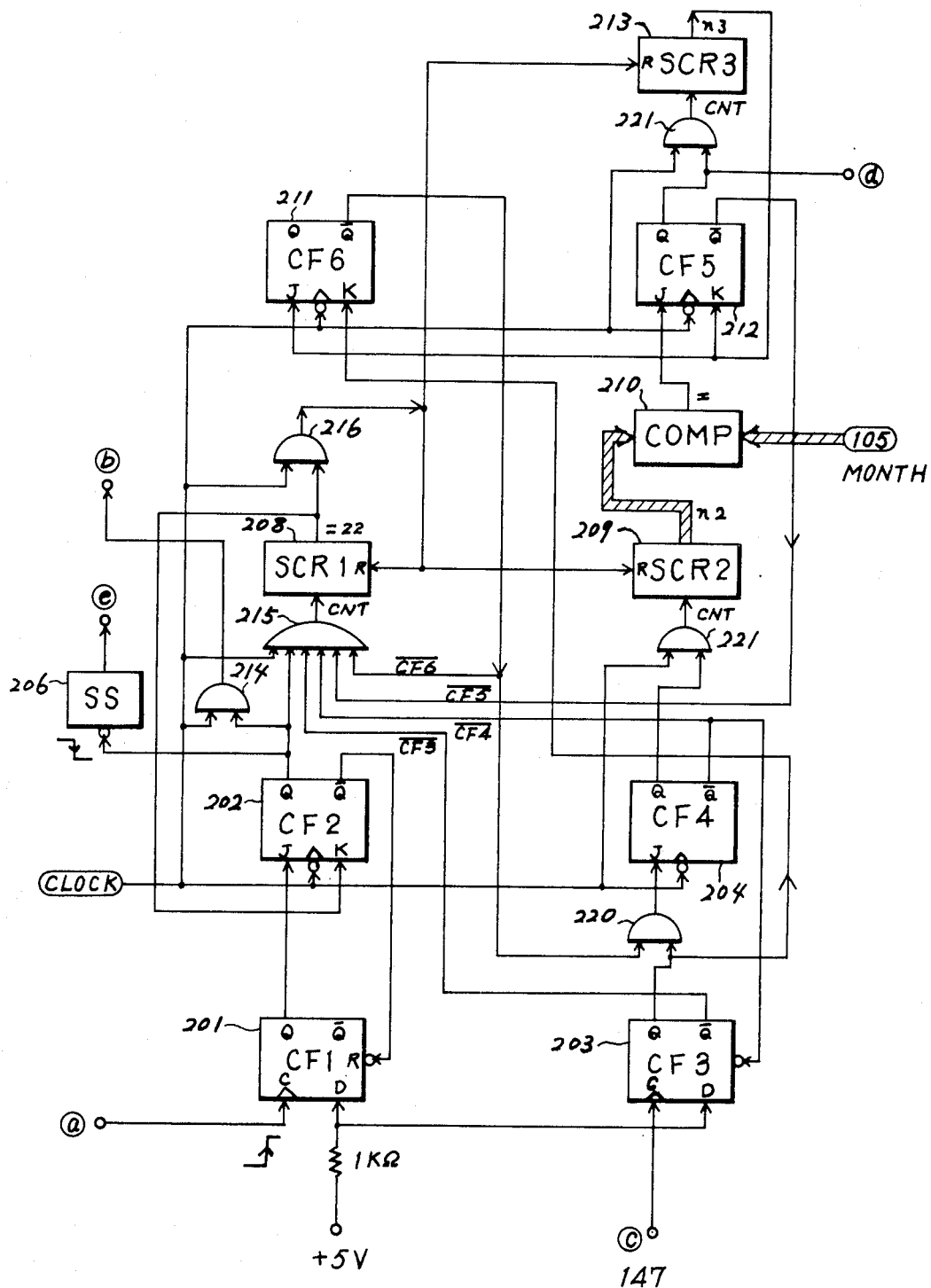
FIG. 10 is a block diagram showing the marking embodiment.

The operations are mentioned in FIG. 12 and the timings of the block diagram illustrated in FIG. 10 are shown in FIG. 11. The reference symbols (a) to (e) mentioned above are inserted in FIGS. 10 and 11 for easy understanding of the operations.

Prior to discussing the block diagram, we will explain a concept of this embodiment.

The marking for specifying the month now being drawn up is recorded with the ball point pen 60 which is used to draw up the physical rhythm chart. As an operational procedure, there is provided a counter of modulo 23 which corresponds to the physical rhythm with a period of 23 days and a paper feeding motion is interrupted when the hole 13 perforated in the recording paper 10 is detected. At the same time, all the other logics are inhibited. The ball point pen 60 (disc 5-1) is set at the starting position for drawing up the chart for June, for example. The position of disc 5-1 under this condition is defined as a number of pulses $n1$ calculated in terms of pulses from the position of $+0$.

Next, the disc 5-1 begins to rotate and the counter 208 starts to count from the starting position of $n1$ in coincidence with the rotation of the disc 5-1. The counting of counter 208 is interrupted at the time when the slit 40-1 on disc 5-1 is detected by photoconductive cell 41-1. In other words, that timing means that the ball point pen 60 reaches the position of $+0$. It wil be apparently understood that a compliment of value $n1$ against modulo 23 is calculated in terms of pulses from the starting position.

Next, the disc 5-1 is rotated until the ball point pen 60 reaches the month now being drawn up. There is provided a counter 209 with modulo 23 and comparator 210. A number of pulses which determine a distance for the disc 5-1 to rotate so as to arrive at the June position is set in the comparator 210. The counter counts in coincidence with the rotation of disc 5-1 which is interrupted in its rotation when the ball point pen 60 reaches June. In other words, the interruption occurs when a coincidence with the value n2 from the digital switch 105 and the output of counter 209 is obtained. Then, the ball point pen 60 contacts the recording paper 10. There is provided a counter 213 which counts up to n3 which rotates the disc 5-1 so that the ball point pen will mark a predetermined length marking for June. When the counter 213 counts up to n3, the ball point pen 60 is pulled up from the recording paper 10.

Then, the disc 5-1 is successively rotated and same returns to the starting position for this operation when the slit 40-1 is detected by the photoconductive cell. The returned position of the disc 5-1 is the same position as that of counter 208 which counted the compliment mentioned above.

From that position, the counter starts to count in coincidence with rotation of disc 5-1 and when the counter counts "0, " the disc 5-1 and the ball point pen 60 return to the starting position for drawing up the physical rhythm for June due to the fact that the counter 208 is modulo 23. Then, a single shot 206 is triggered so as to put out a pseudo hole detecting signal thereby removing the inhibited circuit at the first stage for drawing up the biorhythm charts. Those operations are mentioned in FIG. 12.

Further explanation will be given hereinafter concerning FIG. 10 with reference to the operations mentioned above.

(1) When the hole 13 is detected by the photoconductive cell 20, D-type flip-flop 201 is reset by a trailing edge of a signal supplied from the inverting amplifier 152 through the terminal (a).

(2) The D-type flip-flop 201 is reset by a clock which is supplied at first after setting the flip-flop 201 and a JK flip-flop 202 is set by the same clock.

(3) When the JK master-slave flip-flop 202 is set, the counter 208 (SCR1) of modulo 23 is supplied with pulses, under the conditions of $\overline{CF3} \cdot \overline{CF4} \cdot \overline{CF5} \cdot \overline{CF6}$, through an AND circuit 215 with a period of clocks and the counter is activated to count.

(4) When pulse motor 3-1 is rotated, arrival of pin 8-1 at the point of +0 is detected by the photoconductive cell 41-1 and the output of photoconductive cell 41-1 is supplied to the inverting amplifier 147 for setting the D-type flip-flop 203 by the trailing edge of the signal supplied by inverting amplifier 147 so as to obtain an output from the Q side thereof.

An AND circuit 220 is enabled by outputs from the D-type flip-flop 203 and JK master-slave flip-flop 211, thereby setting a JK master-slave flip-flop ($\overline{CF4}$). The output of JK master-slave flip-flop 204 is logically anded by the AND circuit 221 with clocks and then the anded output of the JK master-slave flip-flop 204 is supplied to the counter 209 (SCR2).

(5) Then, the counter starts to count the outputs of the JK master-slave flip-flop 204.

(6) The counter continues its counting until it reaches n2. The comparator 210 is set at the value n2 by the digital switch 105. Accordingly, when a counted value of counter 209 reaches n2, an output from comparator 210 is obtained.

(7) By the output of comparator 210, a JK master-slave flip-flop 212 is set. At this time, the output of JK master-slave flip-flop 212 is amplified by the plunger driver 143, thereby energizing the coil 61 and pushing out the ball point pen 60 for marking the specified month.

(8) When the JK master-slave flip-flop 212 is set, a predetermined value n3 is stored in a counter 213 (SCR3) to allow time to energize the coil 61 for marking the predetermined length of marking.

The output of JK master-slave flip-flop 212 is logically anded with the clock by the AND circuit 221 and then the output is supplied to the counter 213 (SCR3).

(9) The counter counts up a predetermined number of pulses, the JK master-slave flip-flop 212 is reset by the output of JK master-slave flip-flop 213 and at the same time, JK master-slave flip-flop 211 ($\overline{CF6}$) is set.

(10) Q side output of the JK master-slave flip-flop 202 is logically anded with the clock by an AND circuit 214 and then the output is supplied to the pulse motor 3-1 for rotation of disc 5-1. By that rotation, the slit 40-1 arrives below the photoconductive cell 41-1 and is detected thereby. When detected, JK master-slave flip-flop 211 is reset by the trailing edge of the output of the inverting amplifier 147. Thus, the conditions of $\overline{CF3} \cdot \overline{CF4} \cdot \overline{CF5} \cdot \overline{CF6}$ are satisfied. The counter 208 is initiated in its recounting from the value previously set.

(11) When the counter 208 counts up to "0, " all counters provided in FIG. 10 are reset and the single shot 206 (SS6) is triggered by the trailing edge of the output of JK master-slave flip-flop 202.

(12) The output of single shot 206 is supplied to the terminal "e" as a pseudo hole detection signal for initiating the operations mentioned in FIG. 7.

(13) The output of JK master-slave flip-flop 202 inhibits outputs of clock generator 112, paper feeding clock generator 116 and inverting amplifier 147 and also controls the rotation of pulse motor 3-1.

From the foregoing, it can be clearly understood that marking on the month to be drawn up on the chart can be successfully carried out and achieved as illustrated in FIG. 13.

The invention consists of the construction hereinbefore fully described, illustrated in the accompanying drawings and set forth in the claims hereto appended, it being understood that various changes in the operation, proportion and minor details of construction, within the scope of the claims, may be changed without departing from the spirit of the invention or sacrificing any of the advantages thereof.

What is claimed is:

1. A biorhythm chart drawing-up apparatus comprising digital switches for setting a date for the birthday of an examinee, a date for examination and a number of months to be recorded monthly, pulse motors provided in association with a physical rhythm, a rhythm of sentiment and a rhythm of intellect, said pulse motors rotate in association with respective periods, discs respectively coupled to an axis of each of said pulse motors, pins eccentrically extending from the center of respective said discs, converting means for converting circular motions of said pulse motors into reciprocating motions by T-shaped piston rods provided with slits for guiding said pins, guide members for guiding said piston rods, plungers provided with ball point pens contactedly movable on a recording paper, respectively fixed to said piston rods, a control unit for storing data put in by said digital switches, said control unit calculates respective guide numbers for respective biorhythms and provides a number of pulses corresponding to the guide number for placing said ball point pen at a starting point for drawing up a biorhythm chart, a feeding means for feeding said recording paper up to a distance determined by said digital switch for setting the number of months to be recorded, a first start controlling means, for detecting a reference position, provided in said recording paper, at a time of drawing up said chart for the first date in a month, which date arrives at a position below a first ball point pen positioned in a feeding direction and above said recording paper so as to initiate rotation of said pulse motor corresponding to the period of physical rhythm and energize said plunger to have said ball point pen contact said recording paper for drawing up said chart, a second start controlling means for initiating rotation of said pulse motor corresponding to a period of rhythm to be recorded and energize one of said plungers to have a second of said ball point pens contact said recording paper for drawing up said chart at a time when said first date in the month arrives below said second ball point pen arranged in a second position in the feeding direction of said recording paper, a third start controlling means for initiating rotation of said pulse motor corresponding to a period of rhythm to be recorded and energize one of said plungers to have a third of said ball point pens contact said recording paper for drawing up said chart at a time when said first date in the month arrives below said third ball point pen arranged in a third position in the feeding direction of said recording paper, operation interruption means respectively combined with said start controlling means for interrupting rotations of said pulse motors and deenergizing said plungers upon completion of drawing said charts per one month, thereby continuing the feeding of said recording paper up the point of obtaining a feeding length specified by said input data from said digital switches and when detection of said reference position provided in said recording paper for the next month is carried out, the operation is repeated and detection of said reference position is carried out until completion of drawing up said chart for a number of months specified by said digital switches and thereafter, the feeding of said recording paper is stopped.

2. A biorhythm chart drawing-up apparatus as claimed in claim 1, wherein, an inhibiting means for inhibiting a clock for feeding said recording paper, a clock from a clock generator and an output of an inverting amplifier put out outputs upon detection of a zero position of a rotation angle of said disc, the first counter which counts a number of pulses to rotate said pulse motor so as to allow said ball point pen to arrive at said zero position from a previously set position to start drawing up said chart and said first counter ceases its counting when said ball point pen reaches said zero position, a second counter, initiated in its counting at the time when said ball point pen arrives at said zero position, sends pulses to said pulse motor so that said ball point pen arrives at a mark of a month to be recorded while comparing a value set in a counter latch circuit by said digital switch and at a time of coincidence when a counted value and said value set in said counter latch circuit is obtained, a plunger driver energized so as to contact said ball point pen with said recording paper, a third counter which sends a predetermined number of pulses to said pulse motor for causing said ball point pen to mark a predetermined length of marking on said recording paper for specifying the name of a month to be recorded thereon and when said predetermined number of pulses is counted, said plunger driver is deenergized so as to remove said ball point pen from the surface of said recording paper, thereby rotation of said pulse motor being continued in its rotation and at the time when said ball point pen again reaches said zero position, said first counter restarts its counting value up to a time when said value again becomes zero and said inhibitions are removed and a single shot is triggered so as to place said biorhythm chart drawing-up apparatus in a ready condition for drawing up said chart.

3. A biorhythm chart drawing-up apparatus as claimed in claim 1, wherein a ball point pen holder provided with a plunger is constructed so as to form an axially elongated hollow cylinder, a first coil spring wound around said plunger from a sole member of said ball point pen holder for pushing said plunger in the counter direction of operation, a second coil spring wound around said ball point pen so that said ball point pen is pushed out past the exterior of said pen holder via said hollow cylinder so as to elastically contact said ball point pen with said recording paper, thereby while drawing up said chart by applying current to a solenoid to maintain said first coil spring in a depressed state for elastically contacting said ball point pen with said recording paper, contact pressure is controlled by said second coil spring.

* * * * *